(12) United States Patent
Plantamura et al.

(10) Patent No.: US 12,076,350 B2
(45) Date of Patent: Sep. 3, 2024

(54) FECAL MICROBIOTA COMPOSITION FOR USE IN REDUCING TREATMENT-INDUCED INFLAMMATION

(71) Applicant: MaaT PHARMA, Lyons (FR)

(72) Inventors: Emilie Plantamura, Lyons (FR); Cyrielle Gasc, Lyons (FR); Benoît Levast, Lyons (FR); Lilia Boucinha, Lyons (FR); Corentin Le Camus, Lyons (FR); Carole Schwintner, Lyons (FR); Hervé Affagard, Lyons (FR)

(73) Assignee: MaaT PHARMA, Lyons (FR)

( * ) Notice: Subject to any disclaimer, the term of this patent is extended or adjusted under 35 U.S.C. 154(b) by 484 days.

(21) Appl. No.: 17/261,532

(22) PCT Filed: Jul. 19, 2019

(86) PCT No.: PCT/EP2019/069597
§ 371 (c)(1),
(2) Date: Jan. 19, 2021

(87) PCT Pub. No.: WO2020/016445
PCT Pub. Date: Jan. 23, 2020

(65) Prior Publication Data
US 2021/0299188 A1  Sep. 30, 2021

(30) Foreign Application Priority Data

Jul. 20, 2018 (EP) ..................................... 18305997
Mar. 8, 2019 (WO) .................. PCT/FR2019/050522

(51) Int. Cl.
*A61K 35/74* (2015.01)
*A61K 35/38* (2015.01)

(52) U.S. Cl.
CPC .............. *A61K 35/74* (2013.01); *A61K 35/38* (2013.01)

(58) Field of Classification Search
CPC ................................. A61K 35/74; A61K 35/38
See application file for complete search history.

(56) References Cited

U.S. PATENT DOCUMENTS

| | | | | |
|---|---|---|---|---|
| 2018/0296582 A1* | 10/2018 | von Maltzahn | ...... | A61K 31/047 |
| 2019/0032004 A1* | 1/2019 | Subhadra | .................. | C12N 7/00 |
| 2022/0023356 A1* | 1/2022 | Borody | .................. | A61K 35/74 |

FOREIGN PATENT DOCUMENTS

| | | |
|---|---|---|
| WO | 2012016287 A2 | 2/2012 |
| WO | 2016170285 A1 | 10/2016 |
| WO | 2016170290 A1 | 10/2016 |
| WO | WO 2016/170285 A1 * | 10/2016 |
| WO | 2017103550 A1 | 6/2017 |
| WO | WO 2019/227085 A1 * | 11/2019 |

OTHER PUBLICATIONS

Barazzuol et al. Molecular Oncology, 2020; 14:1538-1554 (Year: 2020).*
Felman, Medical News Today, https://www.medicalnewstoday.com/articles/248423#types-and-symptoms; accessed on Apr. 21, 2023 (Year: 2023).*
Barhum, https://www.verywellhealth.com/what-is-inflammation-187934, updated Nov. 29, 2022 (Year: 2022).*
Mohty, Mohamad, et al., Prevention of Dysbiosis Complications with Autologous Fecal Microbiota Transplantation (auto-FMT) in Acute Myeloid Leukemia (AML) Patients Undergoing Intensive Treatment (ODYSSEE study): First Results of a Prospective Multicenter Trial, retrieved at: http://www.bloodjournal.org/content/130/Suppl_1/2624, Dec. 7, 2017, 3 pages.
Wang, Yinghong, et al., P038 Fecal Microbiota Transplant (FMT) for Immuno-Checkpoint Inhibitor-Induced Colitis (ICI-C) in a 50 Year Old Female With Bladder Cancer, Inflammatory Bowel Diseases, vol. 24, Feb. 2018, retrieved at http://dx.doi.org/https://doi.org/10.1093/ibd/izy019.043, 2 pages.
Le Bastard, Quentin, et al., Fecal microbiota transplantation reverses antibiotic and chemotherapy-induced gut dysbiosis in mice, Scientific Reports vol. 8, Article No. 6219 (2018), retrieved at http://dx.doi.org/10.1038/ $41598-018-24342-x, 12 pages.
Cui, Ming, et al., Faecal microbiota transplantation protects against radiation-induced toxicity, EMBO Molecular Medicine, vol. 9, Issue 4, Apr. 1, 2017, retrieved at http://dx.doi.org/10.15252/emmm.201606932, 14 pages.
Maat Pharma, Interventional Study of Bone and Joint Infections Related Gut Dysbiosis (OSIRIS), posted Apr. 5, 2018, retrieved at https://clinicaltrials.gov/ct2/show/study/NCT03011502, 6 pages.
Gundling, F., et al., Successful autologous fecal transplantation for chronic diversion colitis, Techniques in Coloproctology vol. 19, retrieved at http://dx.doi.org/10.1007/s10151-014-1220-2, 1 page. Not a complete document.
Bak, Seon Ho, et al., Fecal microbiota transplantation for refractory Crohn's disease, Intestinal Research 2017;15, retrieved at http://dx.doi.org/10.5217/ir.2017.15.2.244, 7 pages.
Rossen, Noortje G., et al., Fecal microbiota transplantation as novel therapy in gastroenterology: A systematic review, World J Gastroenterol. May 7, 2015; 21(17), retrieved at http://dx.doi.org/10.3748/wjg.v21.i17.5359, 14 pages.
Tian, Zhihui, et al., Beneficial Effects of Fecal Microbiota Transplantation on Ulcerative Colitis in Mice, Digestive Diseases and Sciences vol. 61 (2016), retrieved at http://dx.doi.org/10.1007/s10620-016-4060-2, 1 page. abstract.
International Search Report for PCT/EP2019/069597, dated Oct. 21, 2019, 6 pages.

(Continued)

*Primary Examiner* — Brian Gangle
*Assistant Examiner* — Lakia J Jackson-Tongue
(74) *Attorney, Agent, or Firm* — ARENTFOX SCHIFF LLP

(57) ABSTRACT

The invention relates to the use of fecal microbiota transplant for preventing and/or reducing systemic and gut treatment-induced inflammation in an individual in need thereof.

19 Claims, 9 Drawing Sheets

(56) References Cited

OTHER PUBLICATIONS

Figure 1:
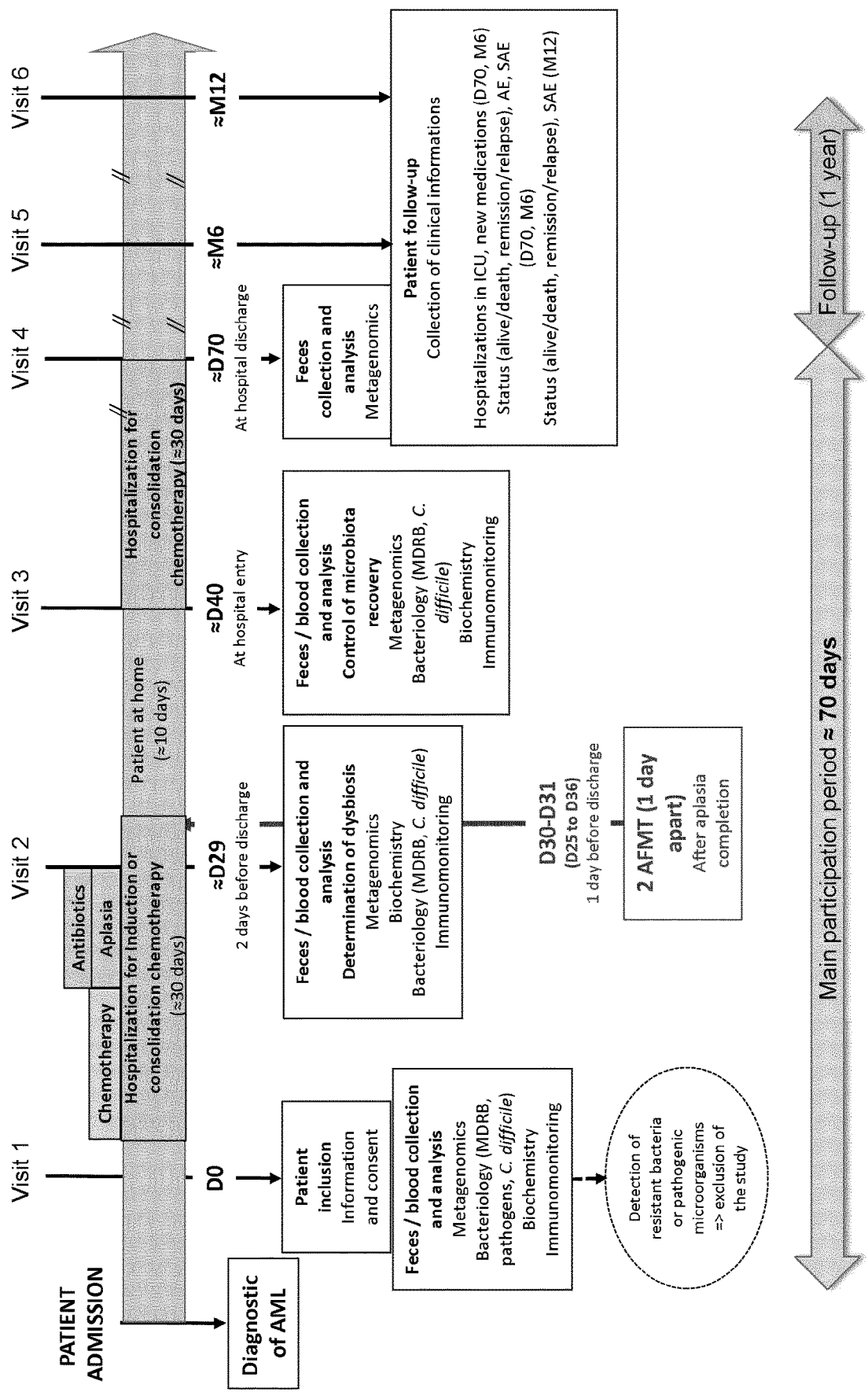

Perales-Puchalt et al., "Microbiota Reconstitution Restores Intestinal Integrity After Cisplatin Therapy," Journal of Leukocyte Biology, May 2018, vol. 103, No. 5, pp. 799-805.

Spindelboeck et al., "Repeated fecal microbiota transplantations attenuate diarrhea and lead to sustained changes in the fecal microbiota in acute, refractory gastrointestinal graft-versus-host-disease," Haematologica, 2017, vol. 102, pp. e210-e213.

* cited by examiner

FECAL MICROBIOTA COMPOSITION FOR USE IN REDUCING TREATMENT-INDUCED INFLAMMATION

CROSS-REFERENCE TO RELATED APPLICATIONS

This application is a National Stage of PCT/EP2019/069597, filed on Jul. 19, 2019, which claims priority to European Patent Application No. 18305997.1, filed on Jul. 20, 2018, and International Application No. PCT/FR2019/050522, filed on Mar. 8, 2019, the disclosures of which are herein incorporated by reference in their entireties.

FIELD OF THE INVENTION

The present invention relates to the field of anti-cancer therapy or other therapies needing treatments that provoke local or systemic inflammation, and provides means and compositions for preventing and/or reducing iatrogenic inflammation, thereby reducing adverse events.

BACKGROUND AND PRIOR ART

Acute myeloid leukemia (AML) is a relatively rare but potentially fatal blood cancer. AML is characterized by an abnormal proliferation of malignant, poorly differentiated myeloid cells within the bone marrow and peripheral blood (Saultz and Garzon, 2016). Standard therapy for AML relies on conventional chemotherapy with or without stem cell transplantation. Eligible patients first undergo an induction phase with intensive chemotherapy. If complete remission is achieved, consolidation therapy is performed to deepen response and achieve long lasting remission. Standard induction and consolidation therapies include one or several cycles of intensive chemotherapy and/or hematopoietic stem cell transplantation (HSCT) depending on risk profiles in the patient (Döhner, Weisdorf and D, 2015). The different treatment phases of AML require prolonged hospital stays in a protected environment and multiple courses of antibiotic treatments due to the high risk of life-threatening infectious complications (Mayer et al., 2015).

Such treatments have been demonstrated to dramatically alter the composition of the human gut microbiota (Galloway-Pena et al., 2016; Galloway-Peña et al., 2017). The induced so-called dysbiosis is characterized by a reduction of overall microbial diversity, a disruption of beneficial bacteria that support host defences, and a rise in dominance of bacterial species usually subdominant, including some pathogens and pathobionts and multidrug-resistant (MDR) bacteria (Jandhyala et al., 2015; Montassier et al., 2015). Thus, chemotherapy and antibiotic treatment disrupt the mutualistic relationship between host and microorganisms and promote pathological conditions involving uncontrolled local immune responses and potentially systemic inflammation (Palm, Zoete and Flavell, 2015).

Recent studies demonstrated that a high gut microbial diversity is associated with improved clinical outcome and reduced infectious complications in patients (Galloway-Pena et al., 2016; Galloway-Peña et al., 2017; Malard et al., 2018). A significant decrease in microbial diversity over the course of induction chemotherapy was observed in stool samples from AML patients. Moreover, induction chemotherapy is known to have dramatic consequences on the gastrointestinal epithelium, leading to colitis with severe abdominal pain, diarrhea, hematochezia with evidence of bowel inflammation (Hogan et al., 2002; Camera et al., 2003). The systemic inflammatory status of AML patients was shown to be significantly increased after induction chemotherapy, as measured with two serum markers of inflammation: C-Reactive Protein (CRP) and ferritin levels (Khitam A W Ali, Alaa F Alwan, 2015). The intestinal consequences of AML treatments can thus interfer with the patient's optimal care: increase of infectious-related complications (e.g. sepsis), bad nutrition status, longer duration of hospitalization, interruption or delayed consolidation courses due to treatment toxicity (Elting et al., 2003).

There is a need to develop therapeutic solutions to alleviate gut inflammation that has been induced by anti cancer treatment in AML patients.

The development of strategies such as fecal microbiota transfer (FMT) to restore the diverse microbial communities lost during disease treatment, and consequently to suppress or decrease treatment-related complications in AML patients, could offer novel therapeutic possibilities (Khanna, 2018; Malard et al., 2018) Khanna 2017). The purpose of the single arm prospective clinical trial reported in Example 1 was to use autologous FMT (AFMT) in AML patients treated with intensive chemotherapy and antibiotics in order to restore their gut microbiota diversity and reduce treatment-induced MDRB carriage. Surprisingly, the inventors also showed that FMT in AML patients leads to a decrease of inflammation, especially local intestinal inflammation. A description of the clinical protocol of this trial (named ODYSSEE) was published by Mohty et al. ["Prevention of Dysbiosis Complications with Autologous Fecal Microbiota Transplantation (auto-FMT) in Acute Myeloid Leukemia (AML) Patients Undergoing Intensive Treatment (ODYSSEE study): First Results of a Prospective Multicenter Trial", Blood, 7 Dec. 2017 eA17-12-07]. Neither the method of fecal microbiota sample preparation nor the results of the trial were disclosed in this document.

A number of publications disclose the use of FMT in the treatment of chemotherapy induced gut dysbiosis. For example, Wang et al: "P038 Fecal Microbiota Transplant (Fmt) For Immunocheckpoint Inhibitor-Induced Colitis (ICI-C) in 50 Year Old Female with Bladder Cancer", Inflammatory Bowel Diseases, vol. 24, no. 51, 18 Jan. 2018 (2018-01-18), page S13, Le Bastard et al: discloses "Fecal microbiota transplantation reverses antibiotic and chemotherapy-induced gut dysbiosis in mice", Scientific Reports, vol. 8, no. 1, 18 April 201 8 (201 8-04-1 8), and Cui et al: "Faecal microbiota transplantation protects against radiation-induced toxicity", EMBO Molecular medicine (online), vol. 9, no. 4, 27 Feb. 2017 (2017-02-27), pages 448-461.

In view of the continuing prevalence of cancer today, in particular AML, there is a need to provide reliable, reproducible and efficacious therapeutic solutions that are complementary to, or extend the efficacy of, or reduce side effects of existing AML treatments. Of course, such therapeutic solutions should be suitable for use in patients, in particular, in a fragile population, such as those having cancer.

Specifically, there is a need to provide therapeutic solutions that meet current pharmaceutical requirements, in terms of safety and efficacy. There is a need that such therapeutic products may be produced using processes that are compliant with Good Manufacturing Practice (GMP).

SUMMARY OF THE INVENTION

The present invention pertains to the use of a fecal microbiota composition, for preventing and/or reducing a treatment-induced inflammation in an individual in need thereof.

According to one embodiment of the invention, the microbiota composition has been obtained by a process comprising the steps of:
(i) collecting a stool sample and putting it in anaerobic conditions at most 5 minutes after collection;
(ii) still in anaerobic conditions, mixing the sample with an aqueous saline solution comprising at least a cryoprotectant and/or a bulking agent; and
(iii) filtering the diluted sample.

According to one embodiment of the invention, the fecal microbiota composition comprises microbiota from at least two, or at least three or at least four stool samples from the same individual.

According to one embodiment of the invention, the fecal microbiota composition comprises microbiota obtained from at least one fecal sample from the individual in need of a treatment for reducing inflammation.

According to one embodiment of the invention, the fecal microbiota composition is used in preventing and/or reducing a treatment-induced gut inflammation in an individual in need thereof.

According to one embodiment of the invention, the fecal microbiota composition is used in preventing and/or reducing inflammation induced by an anti-cancer therapy, including chemotherapy.

According to one embodiment of the invention, the preventing and/or reducing said inflammation is carried out by performing at least one FMT 1 to 30 days after the end of the anti-cancer therapy. Preferably, two FMTs may be performed in a 1-7-day interval.

According to one embodiment of the invention, the fecal microbiota composition leads to a decrease of neopterin in the gut and/or a decrease of CRP and/or ferritin in serum of the patient to be treated.

According to one embodiment of the invention, administration of the fecal microbiota composition leads to an increase of the proportion of beneficial bacteria and a decrease of the proportion of deleterious bacteria in the gastrointestinal tract of the individual being treated.

According to one embodiment of the invention, the proportion of some or all the following 15 genera is increased relative to the level after the end of the anti-cancer therapy: *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*.

According to one embodiment of the invention, the fecal microbiota composition administered comprises microbiota from the following 15 genera: *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*.

According to one embodiment of the invention, said individual to be treated is a cancer patient.

According to one embodiment of the invention, said individual to be treated has an hematologic disease.

According to one embodiment of the invention, said individual to be treated has an acute leukemia.

LEGENDS TO THE FIGURES

Figure 2:
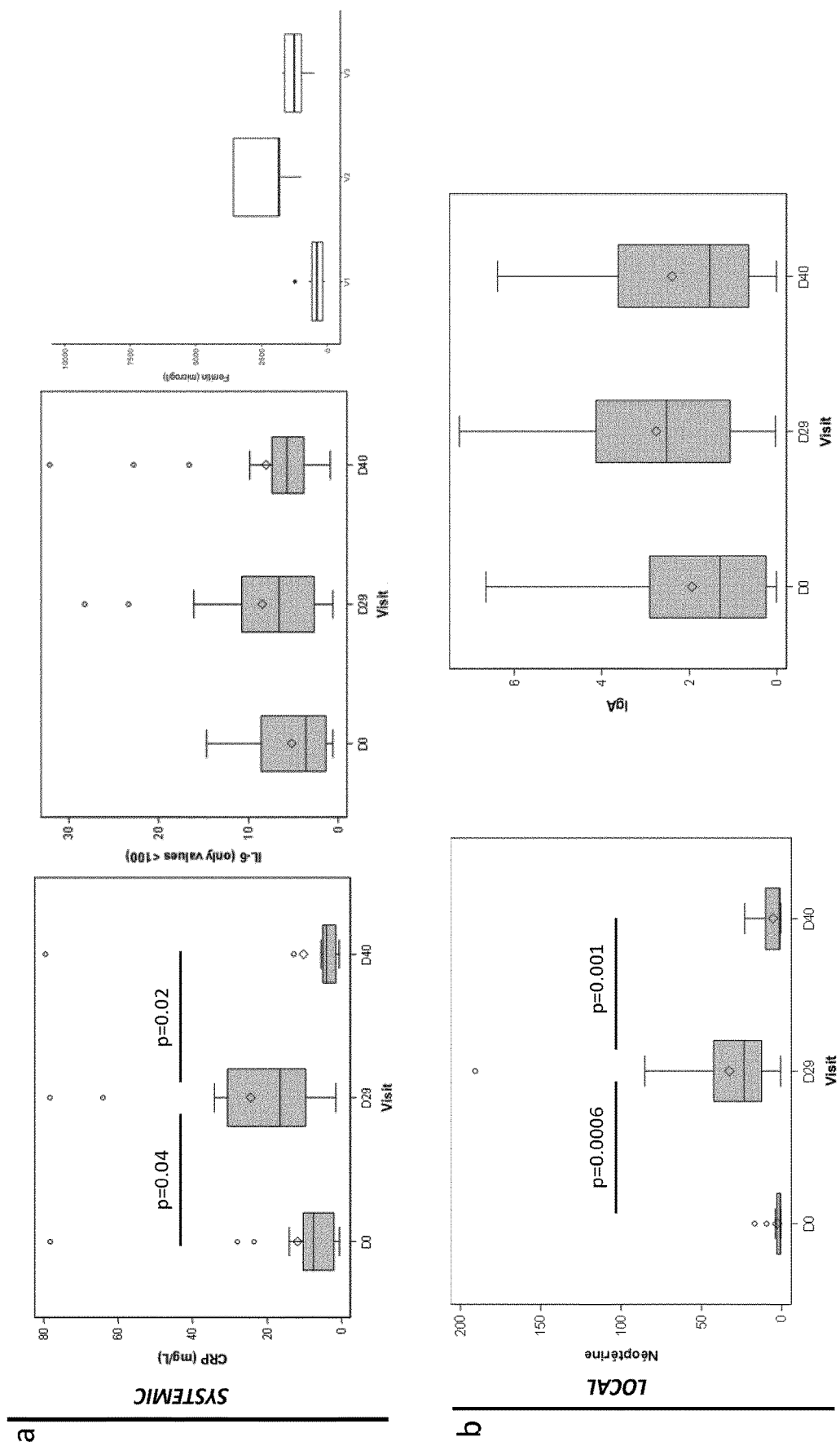
Figure 3:
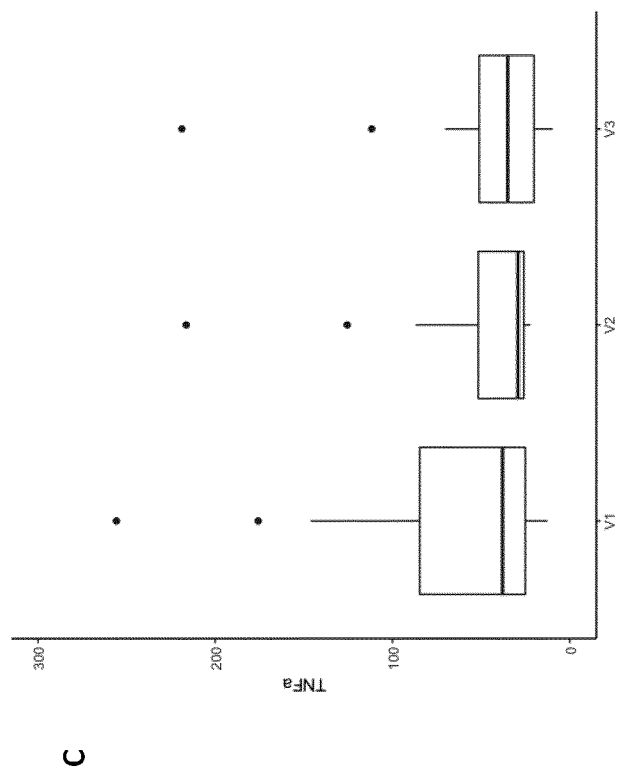
Figure 3:
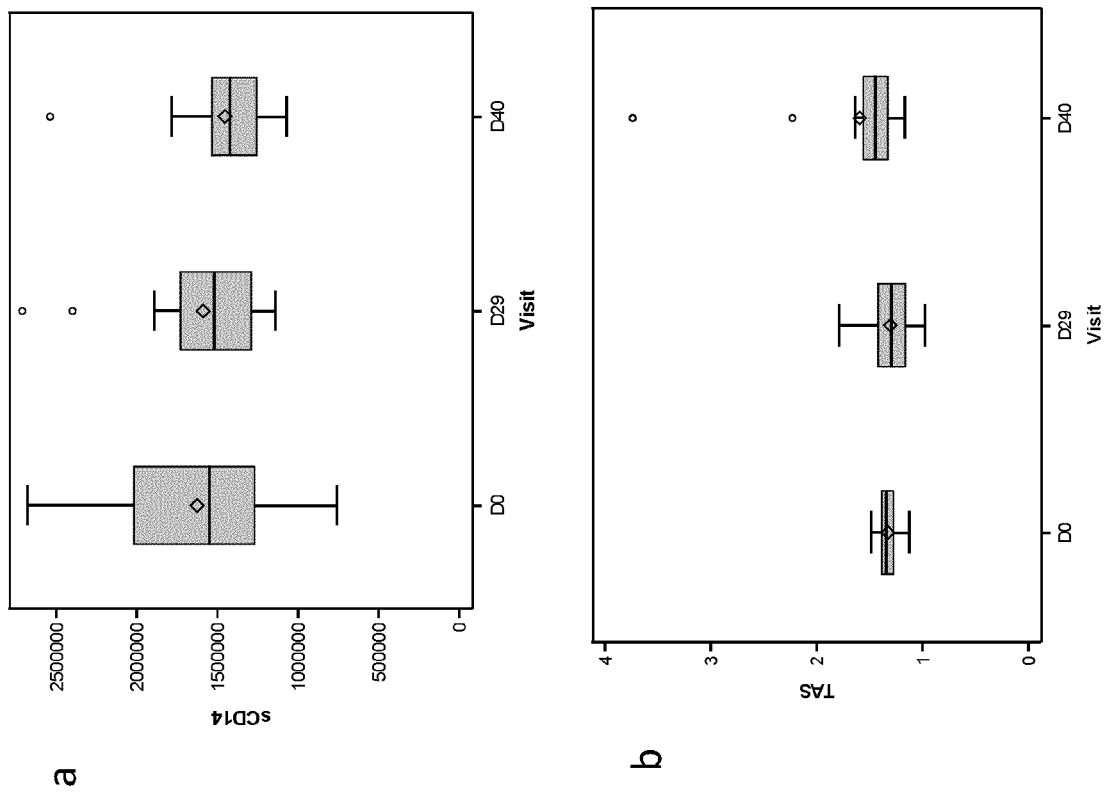
Figure 4:
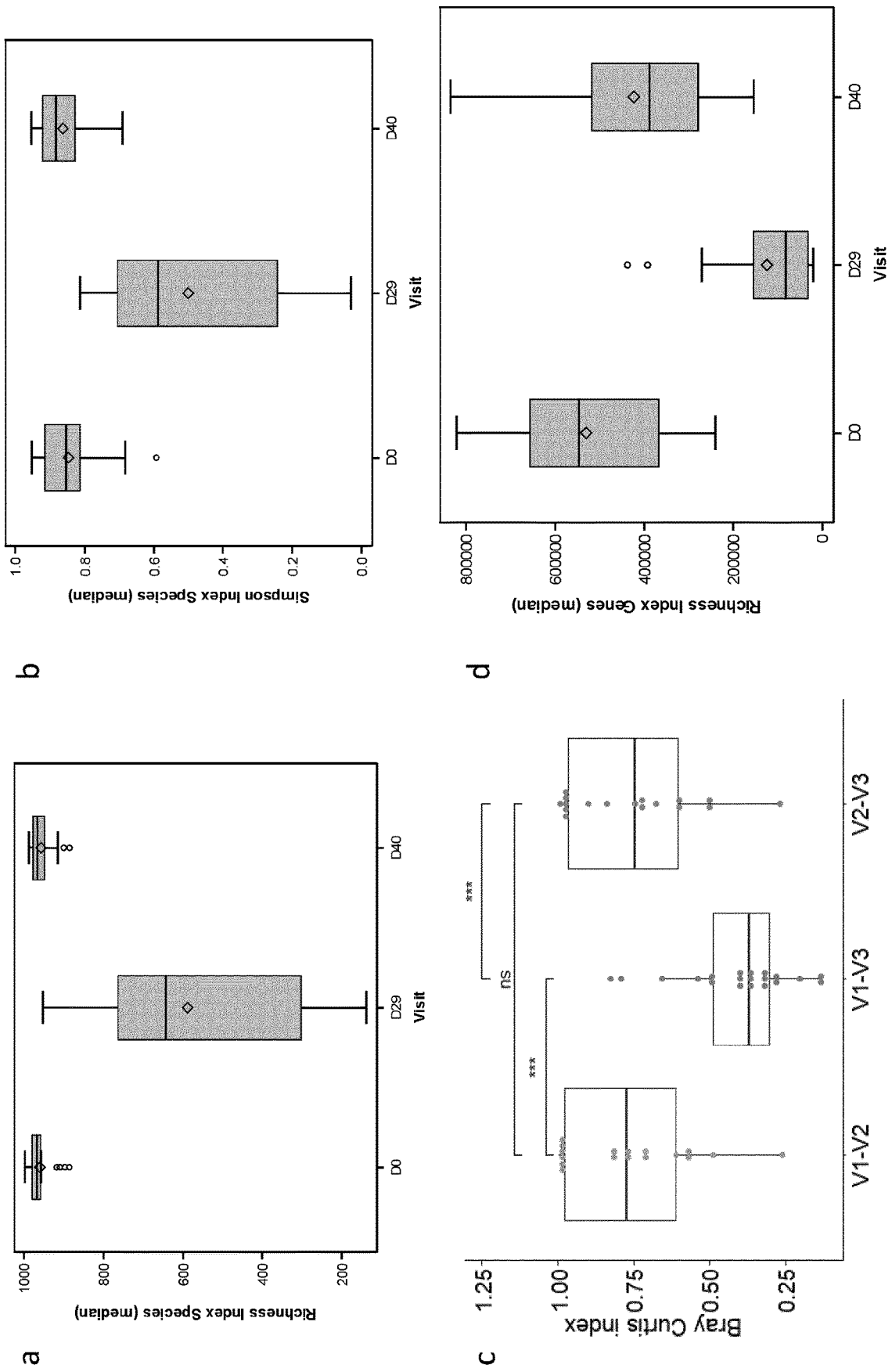
Figure 5:
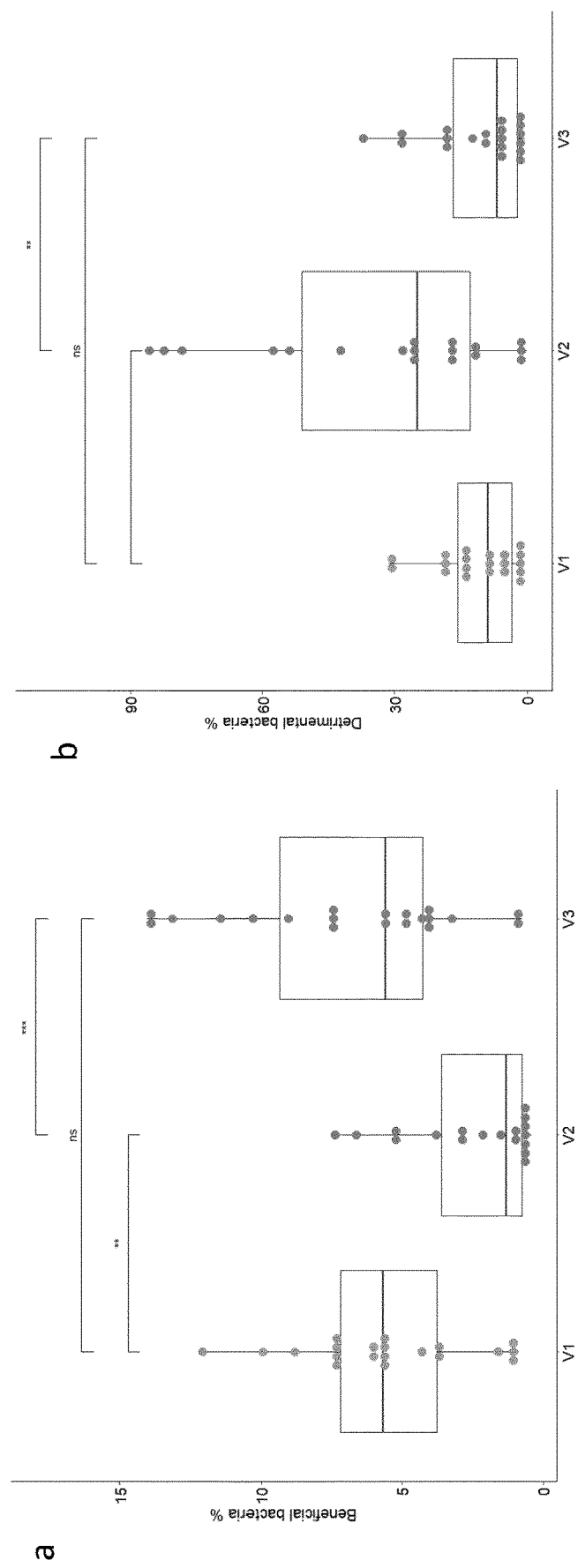
Figure 6:
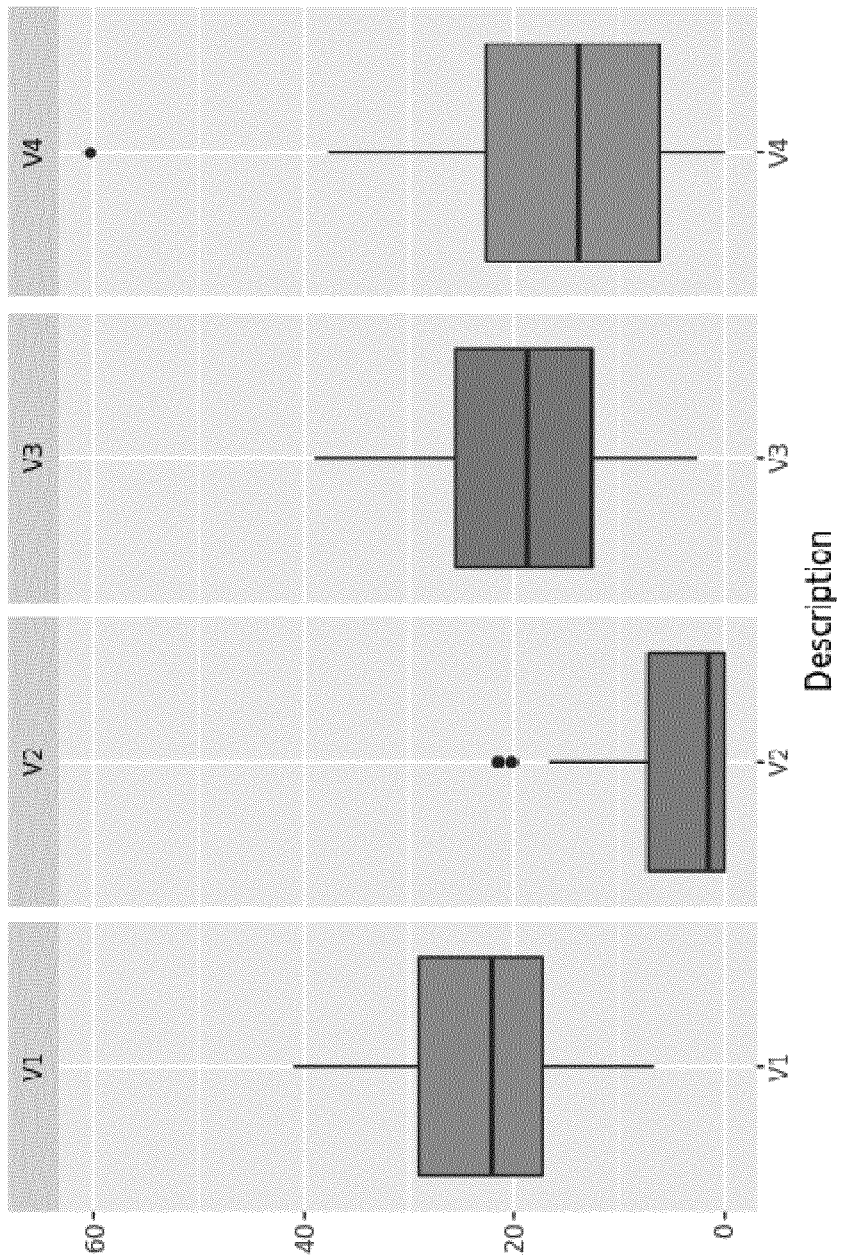
Figure 7:
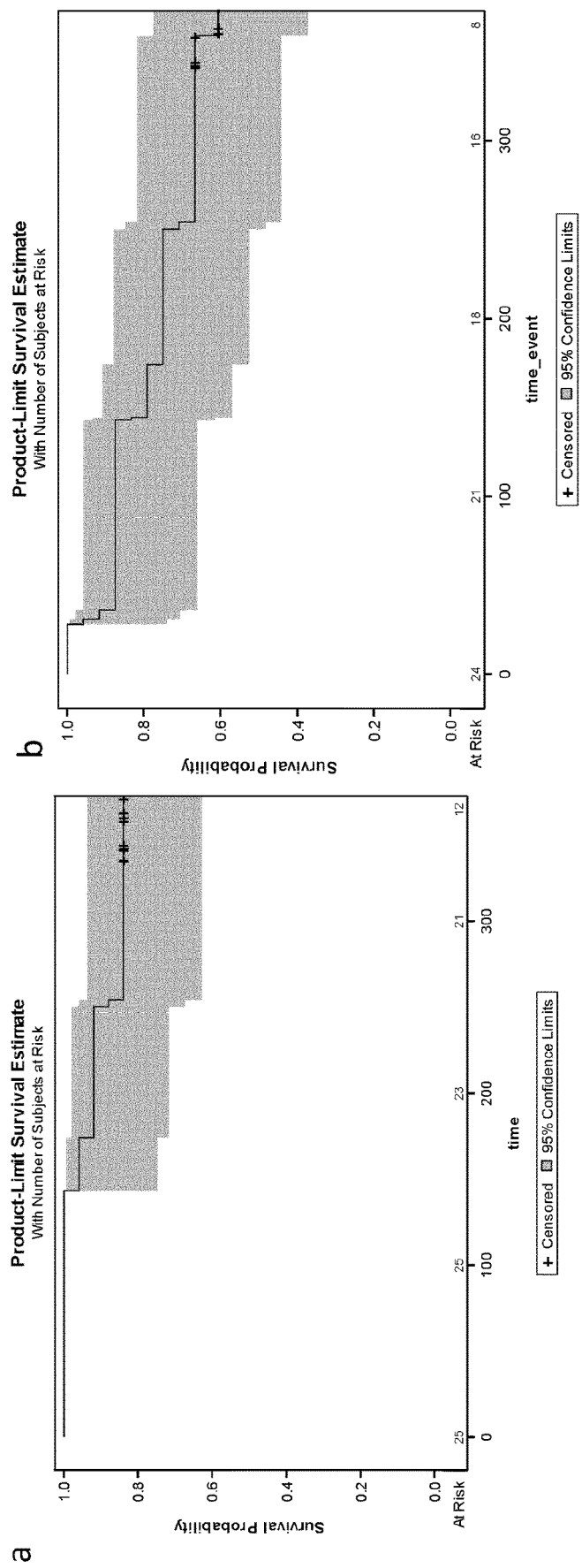
Figure 8:
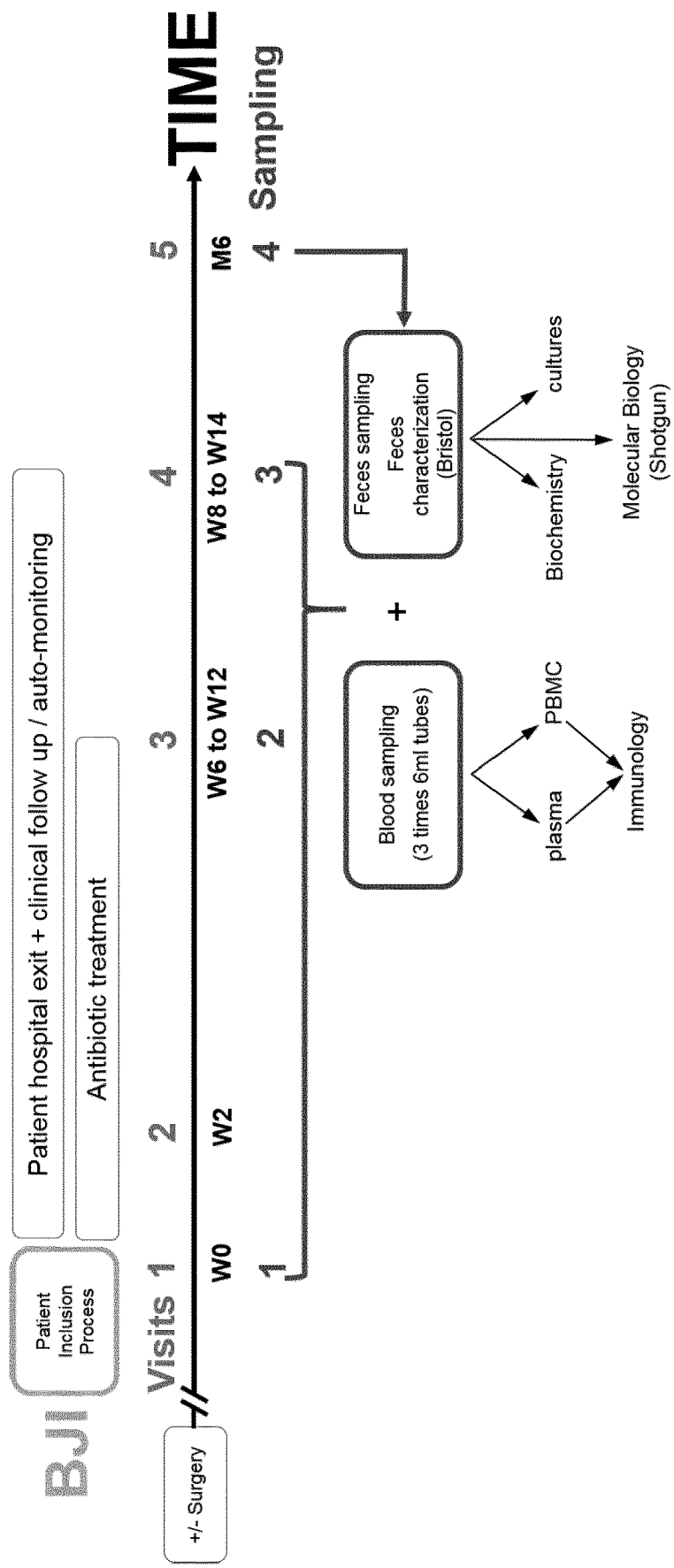
Figure 9:
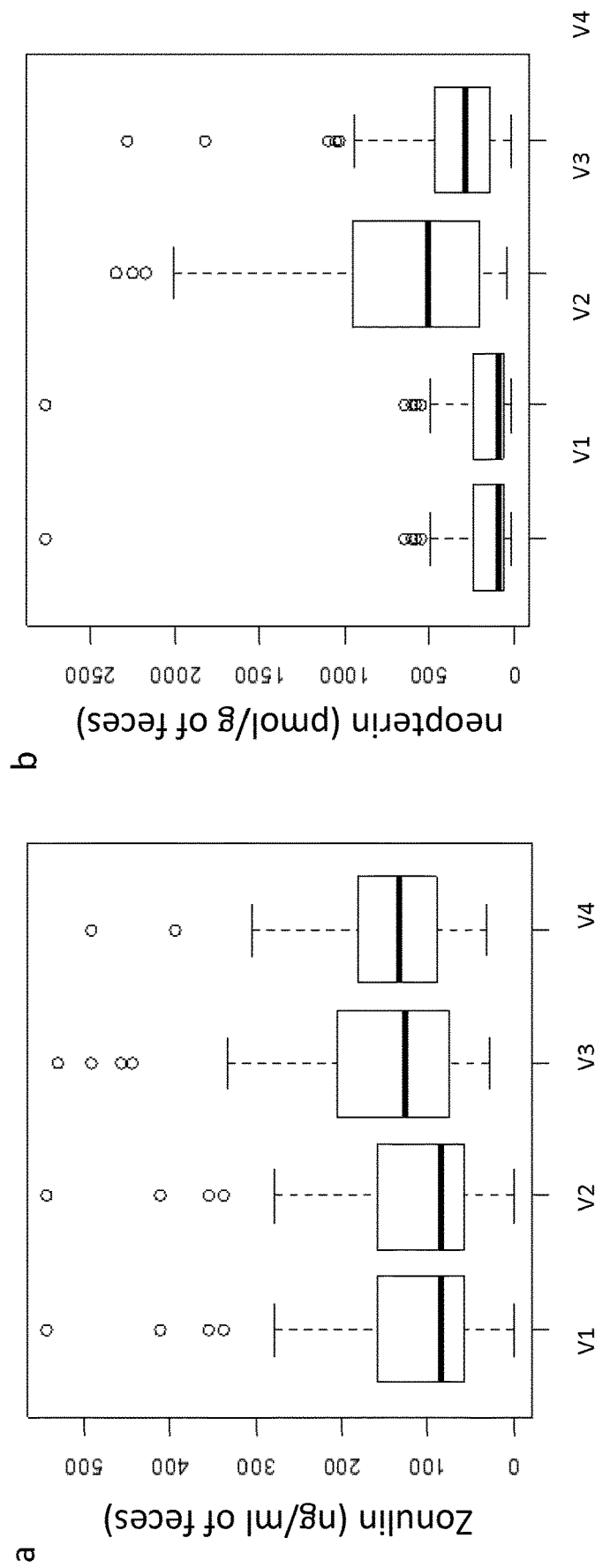

FIG. 1: Odyssee Study Flow chart
FIG. 2: Evolution of biochemical and immunological parameters for the treated population of patients (n=25). (a) Systemic level: IL-6, CRP and ferritin. (b) Local level: neopterin, IgA.
FIG. 3: Evolution of biochemical and immunological parameters for the treated population (n=25) (a) sCD14 (b) TAS (c) TNFα.
FIG. 4: Characterization of the fecal microbiota at AML diagnosis, prior to and following administration of AFMT for the per protocol population (n=20). (a) Species diversity. (b) Simpson index at the species level. (c) Bray Curtis index at the species level. (d) Total number of genes in the microbial community.
FIG. 5: Proportion of beneficial (a) and detrimental (b) bacteria in the microbiota of the per protocole patients (n=20).
FIG. 6: Relative abundance of a selected 15 butyrate generating genera (named "butycore"), namely *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*, in patients in the ODYSSEE study after each of the hospital visits, V1, V2, V3 and V4.
FIG. 7: Survival curves for treated patients. (a) Overall Survival curve. (b) Leukaemia-Free Survival (LFS) curve.
FIG. 8: OSIRIS Study Flow chart.
FIG. 9: Evolution of biochemical and immunological parameters for OSIRIS patients with flow-up (n=42) (a) Zonulin. (b) Neopterin.

DETAILED DESCRIPTION OF THE PREFERRED EMBODIMENTS

In the present text, the following general definitions are used:

Gut Microbiota

The "gut microbiota" (formerly called gut flora or microflora) designates the population of microorganisms (bacteria, archaea, fungi, viruses) living in the intestine of any organism belonging to the animal kingdom (human, animal, insect, etc.). While each individual has a unique microbiota composition, 60 to 80 bacterial species are shared by more than 50% of a sampled human population on a total of 400-500 different bacterial species/individual.

The gut microbiota fulfils similar main physiological functions in all individuals and has a direct impact on the individual's health:
- it contributes to the digestion of certain foods that the stomach and small intestine are not able to digest (mainly non-digestible fibers);
- it contributes to the production of some vitamins (B and K);
- it protects against aggressions from other microorganisms, maintaining the integrity of the intestinal mucosa;
- it plays an important role in the development of a proper immune system;
- a healthy, diverse and balanced gut microbiota is key to ensuring proper intestinal functioning.

Taking into account the major role gut microbiota plays in the normal functioning of the body and the different functions it accomplishes, it is nowadays considered as an "organ". However, it is an "acquired" organ, as intestine colonisation by microorganisms starts right after birth and permanently evolves afterwards throughout the entire life and is the result of different environmental influences (mode of delivery, diet, iatrogenic stress factors . . . ).

While the general composition of the dominant intestinal microbiota is similar in most healthy people (4 main phyla, i.e., Firmicutes, Bacteroidetes, Actinobacteria and Proteobacteria), composition at a species level is highly personalised and largely determined by the individuals' genetic, environment, diet and medical history.

Dysbiosis

Although it can adapt to change and has a high resilience capacity, a loss of balance in gut microbiota composition may arise in some specific situations. This is called "dysbiosis", a deviation to what is considered a "healthy" microbiota in terms of main bacterial groups abundance and diversity (i.e. a disequilibrium between potentially "detrimental" and "beneficial" bacteria in the gut) leading to a disruption of the symbiotic relationship between the host and its microbiota. Dysbiosis may be linked to health problems such as functional bowel disorders, inflammatory bowel diseases, allergies, obesity and diabetes. It can also be the consequence of a medical treatment, such as a cytotoxic treatment (i.e. chemotherapy) or an antibiotic treatment and provoke adverse events such as abdominal pain and diarrhea. Treatment-induced dysbiosis can also favor severe adverse events such as infections and sepsis.

Anti-Cancer Therapy

By "anti-cancer therapy" is herein meant any kind of treatment used to fight cancer, such as chemotherapy, biological therapies (including immunotherapy), radiotherapy and surgery.

Anti-Cancer Chemotherapy

"Chemotherapy" is defined herein as the treatment of cancer with one or more "chemotherapeutic agents". Chemotherapeutic agents are chemical molecules which act by killing cells that divide rapidly, one of the main properties of most cancer cells. Chemotherapy agents include:

alkylating agents such as nitrogen mustards (mechlorethamine, cyclophosphamide, melphalan, chlorambucil, ifosfamide, busulfan etc.) nitrosoureas (N-Nitroso-N-methylurea (MNU), carmustine (BCNU), lomustine (CCNU), semustine (MeCCNU), etc.), tetrazines (dacarbazine, mitozolomide, temozolomide, etc.), aziridines (thiotepa, mytomycin, diaziquone (AZQ), etc.), and non-classical alkylating agents (e.g, procarbazine and hexamethylmelamine);
  spindle poisons such as mebendazole, colchicine;
  mitotic inhibitors (including taxanes (paclitaxel (TAXOL®), docetaxel (TAXOTÈRE®)) and *vinca* alkaloids (e.g.: vincristine, vinblastine, vinorelbine, vindesine)),
  cytotoxic/antitumor antibiotics: such as anthracyclines (e.g.: doxorubicin, daunorubicin, adriamycine, idarubicin, epirubicin and mitoxantrone, valrubicin), *streptomyces* (e.g.: actinomycin, bleomycin, mitomycin, plicamycin)
  anti-metabolites (such as pyrimidine analogues (e.g.: fluoropyrimidines analogs, 5-fluorouracil (5-FU), floxuridine (FUDR), Cytosine arabinoside (Cytarabine), Gemcitabine (GEMZAR®), capecitabine; purine analogues (e.g.: azathioprine, mercaptopurine, thioguanine, fludarabine, pentostatin, cladribine, capecitabine, clofarabine); folic acid analogues (e.g.: methotrexate, folic acid, pemetrexed, aminopterin, raltitrexed, trimethoprim, pyrimethamine),
  topoisomerase inhibitors (e.g.: camptothecins: irinotecan, topotecan, amsacrine, etoposide, etoposide phosphate, teniposide);
  DNA methyltransferase inhibitors: 2'-deoxy-5-azacytidine (DAC), 5-azacytidine, 5-aza-2'-deoxycytidine, 1-[beta]-D-arabinofuranosyl-5-azacytosine, dihydro-5-azacytidine;
  vascular disrupting agents, such as flavone acetic acid derivatives, 5,6-dimethylxanthenone-4-acetic acid (DMXAA) and flavone acetic acid (FAA);
  other chemotherapeutic drugs such as aprepitant, bortezomib (VELCADE®, Millenium Pharmaceuticals), imatinib mesylate (GLEEVEC®), carmustine (BCNU), lomustine (CCNU), tamoxifen, gefitinib, erlotinib, carboxyamidotriazole, efaproxiral, tirapazamine, xcytrin, thymalfasin, vinflunine.

Anti-Cancer Biological Therapies

Anti-cancer "biological therapies" involve the use of living organisms, substances derived from living organisms, or laboratory-produced versions of such substances to treat cancer, by targeting either the cancer cells directly, or by stimulating the body's immune system to act against cancer cells ("immunotherapy"). Biological therapies include monoclonal antibodies (Mabs), including those targeting cancer cell surface (e.g. rituximab and alemtuzumab); antibodies targeting an immune checkpoint such as anti-CTLA4 Mabs (e.g., ipilimumab), anti-PD1 Mabs, anti-PD-L1 Mabs (such as Atezolizumab or Durvalumab), anti-PD-L2 Mabs, anti-Tim3 Mabs, anti-ICOS Mabs etc.; targeting growth factors (e.g.: bevacizumab, cetuximab, panitumumab and trastuzumab); immunoconjugates (e.g.: $^{90}$Y-ibritumomab tiuxetan, $^{131}$I-tositumomab, and ado-trastuzumab emtansine). Other biological therapies include cytokines (including interferons such as IFNα; interleukins such as IL-2, IL-11, G-CSM, GM-CSF), therapeutic vaccines (e.g.: Sipuleucel-T (PROVENGE®)), the bacterium *bacillus* Calmette-Guérin, cancer-killing viruses, gene therapy, and adoptive T-cell transfer.

Anti-Cancer Immunotherapy

"Immunotherapy" herein designates any therapy that acts through the modulation of the immune system of the patient, using biological therapies as described above or any other agent.

Cancer, Treatment, Etc.

As used herein, "cancer" means all types of cancers. In particular, the cancers can be solid or non solid cancers. Non limitative examples of cancers are carcinomas or adenocarcinomas such as breast, prostate, ovary, lung, pancreas or colon cancer, sarcomas, lymphomas, myelomas, melanomas, leukemias, germ cell cancers and blastomas.

Other definitions will be specified below, when necessary.

As described in the experimental part below, the inventors demonstrated that AML patients receiving a fecal microbiota transplant (FMT) after an induction chemotherapy combined with antibiotics not only benefited from restoration of their gut microbiota diversity and reduction of treatment-induced MDRB carriage, but also had a decrease of inflammation, both at the systemic and local intestinal levels. This unexpected result is of tremendous importance, since several adverse events of anti-cancer treatments are related to inflammation.

Hence, according to a first aspect, the present invention pertains to the use of a fecal microbiota composition, for preventing and/or reducing a treatment-induced inflammation in an individual in need thereof.

In the present text, the individual in need of FMT for preventing and/or reducing a treatment-induced inflammation is a human individual or a non-human animal.

In the present text, a "fecal microbiota composition" designates a composition that comprises fecal material with live fecal bacteria, especially a composition suitable for fecal microbiota transplant (FMT). According to a particular embodiment, the fecal microbiota composition comprises the whole microbiota present in a fecal sample or a pool of such microbiota, obtained from different samples.

The inventors have shown that FMT reduces treatment-induced or iatrogenic systemic inflammation, as evidenced by a decrease in the CRP level and/or the ferritin level. This reduction is very beneficial to the patients, since systemic inflammation is known as a cause or risk factor of some severe adverse events (e.g., sepsis) linked to heavy treatments such as anti-cancer treatments. Consistently, the inventors did not observed any sepsis in the AML patients within at least 40 days after receiving a FMT according to the invention. The present invention thus more specifically pertains to the use of a fecal microbiota composition to prevent and/or reduce systemic treatment-induced inflammation and associated complications such as sepsis.

The inventors also demonstrated that FMT reduces local gut inflammation, as evidenced by a decrease in the fecal neopterin level. According to a particular embodiment, the fecal microbiota composition is thus used to prevent and/or reduce gut inflammation and associated gastrointestinal symptoms such as colitis and diarrhea, for example.

According to a particular embodiment of the invention, the fecal microbiota composition used to prevent and/or reduce treatment-induced inflammation has been obtained by a process comprising the steps of:
(i) collecting a stool sample and putting it in anaerobic conditions at most 5 minutes after collection;
(ii) still in anaerobic conditions, mixing the sample with an aqueous saline solution comprising at least a cryoprotectant and/or a bulking agent; and
(iii) filtering the diluted sample, for example at around 265 µm.

According to a preferred embodiment, the aqueous solution used in step (ii) comprises maltodextrine and/or trehalose so that the final concentration (w/vol) of maltodextrine is in the range 5%-15% and/or the final concentration (w/vol) of trehalose is in the range 5%-15%.

Additional optional steps can be added to the above process, such as:
(ia) controlling the stool sample, for example:
  performing a microbiological testing on the sample, to avoid the administration of pathobionts and/or multidrug resistant bacteria (MDRB) to the individual;
  visually assessing the absence of urine and blood in the starting material;
  Bristol stool scaling of the starting material;
  visually assessing the homogeneity and colour of the product, and checking viability of the bacteria present in the sample (by fecal culture).
(iv) pooling several products of step (iii): mixing two or more of said products and homogeneizing the mixture;
(va) freezing the product of step (iii) or (iv) at −80° C.; after thawing, this liquid inoculum will be suitable for administration by enema;
(vb) freeze-drying the product of step (iii) or (iv) using usual freeze-drying materials and protocols. The inoculum lyophilizate is then suitable for administration either by enema in a liquid solution, or orally, in gastro-resistant capsules.
(vc) putting the freezed-dried material of step (vb) in appropriate capsules for oral administration.
(vi) checking the viability and diversity of the bacteria in the product obtained in steps (iii), (iv), (va), (vb) or (vc), and/or the absence of pathobionts and MDRB in said product.

The fecal microbiota composition used according to the present invention can comprise microbiota from one single donor or from several donors. For example, several diluted and filtered samples can be mixed in step (iv) of the above-described process. The skilled in the art will chose, depending on the situation, if it is preferable for the patient to receive a mono-donor FMT (for example, from the patient itself or from a patient's relative) or a multi-donnor FMT.

According to a particular embodiment, the fecal microbiota composition comprises microbiota obtained from a fecal sample from the individual in need of a treatment for reducing inflammation. This embodiment encompasses autologous FMT (AFMT) (i.e., the composition is made from fecal material from this individual only), as well as multi-donnor FMT if the individual's microbiota is pooled with microbiota from at least one other individual.

When autologous FMT is performed in the frame of the present invention, it is preferable to collect stools from the patient before the beginning of the treatment that will induce inflammation and/or dysbiosis, as illustrated in Example 1 below.

According to another particular embodiment, the fecal microbiota composition comprises at least 90% of the genera present in the sample(s) used. In particular, in case of AFMT, the fecal microbiota composition comprises at least 90% of the genera present in the individual's sample collected before the inflammation-inducing treatment.

Anti-cancer treatments usually induce systemic and/or local inflammation, which can be the cause of discomfort and sometimes of severe adverse events (which in turn can result in treatment discontinuation). According to a particular embodiment, the present invention thus pertains to the use of a fecal microbiota composition as above-described, for preventing and/or reducing inflammation induced by an anti-cancer therapy, possibly combined with antibiotherapy and/or hematopoietic stem cell transplantation (HSCT).

According to another particular embodiment, the present invention pertains to the use of a fecal microbiota composition as above-described, for preventing and/or reducing inflammation induced by an antineoplastic agent, possibly combined with antibiotherapy and/or hematopoietic stem cell transplantation (HSCT). "Antineoplastic agents" herein designate any treatment for cancer except surgery. They include chemotherapy, biological therapy including immunotherapy, and radiotherapy.

According to yet another particular embodiment, the present invention pertains to the use of a fecal microbiota composition as above-described, for preventing and/or reducing inflammation induced by chemotherapy, possibly combined with antibiotherapy and/or hematopoietic stem cell transplantation (HSCT).

When performing the invention, the fecal microbiota composition can be administered for fecal microbiota transplant (FMT) before, during and/or after the anti-cancer therapy, for example before, during and/or after a first-line chemotherapy, for example before, during and/or after an induction chemotherapy (such as a "7+3" chemotherapy with cytarabine and an anthracycline antibiotic or daunorubicin).

Several administration regimens can be envisioned in the frame of the present invention. According to a particular embodiment, illustrated in Example 1 below, at least one FMT is performed 1 to 30 days after the end of an anti-cancer therapy, more specifically 20 to 30 days after the end of an induction chemotherapy (which corresponds, for these patients, to the end of antibiotherapy).

According to another particular embodiment, also illustrated in Example 1 below, at least two FMT are performed in a 1- to 7-days interval.

The present invention also pertains to the use of a fecal microbiota composition as above-described, for preventing and/or reducing a treatment-induced inflammation in an individual receiving an anti-cancer treatment, wherein the fecal microbiota composition is administered each day, for example in oral capsules, at cancer diagnosis, before, during and/or after said anti-cancer treatment. According to a particular embodiment, daily uptake of oral capsules comprising the fecal microbiota composition is initiated at the beginning of the induction chemotherapy and is continued during at least 3 to 6 months.

As already mentioned, the inventors demonstrated that FMT leads to a reduction of iatrogenic gut inflammation in the treated patients, evidenced by a decrease of the level of neopterin in the collected stools. According to a particular embodiment of the present invention, FMT with a fecal microbiota composition as above-described leads to a decrease of neopterin in the gut, which can be measured in stool samples from the treated individual. More particularly, the level of neopterin decreases by at least 10%, at least 20%, at least 30% or at least 40%.

The inventors also demonstrated that FMT leads to a reduction of iatrogenic systemic inflammation in the treated patients, evidenced by a decrease of the levels of CRP and/or ferritin in the patients' serum. According to a particular embodiment of the present invention, FMT with a fecal microbiota composition as above-described leads to a decrease of CRP and/or ferritin in the serum of the treated individual. More particularly, the seric level of CRP decreases by at least 10%, at least 20%, at least 30% or at least 40%, and/or the seric level of ferritin decreases by at least 10%, at least 20%, at least 30% or at least 40%.

Another aspect of the present invention is the use of a fecal microbiota composition as described above, for preventing and/or reducing a treatment-induced inflammation in an individual, wherein FMT with said fecal microbiota composition leads to an increase of the proportion of beneficial bacteria and a decrease of the proportion of deleterious bacteria in the gastrointestinal tract.

In the context of the present invention, "beneficial bacteria" include bacteria belonging to the Lachnospiraceae, Ruminococcaceae, Bifidobacteriaceae, Streptococcaceae, Akkermansiaceae, Lactobacillaceae, Eubacteriaceae, Erysipelotrichaceae, Eggerthellaceae, Clostridiaceae, Prevotellaceae, Oscillospiraceae, Rikenellaceae and Odoribacteraceae families, and "deleterious bacteria" include bacteria belonging to the Bacteroidaceae and Enterococcaceae families. According to the invention, a fecal microbiota composition is considered as leading to an increase of the proportion of beneficial bacteria and a decrease of the proportion of deleterious bacteria in the gastrointestinal tract if, between 2 days and 3 weeks after FMT with said composition, the sum of abundances of the beneficial bacteria listed above is superior to that measured just before FMT and the sum of abundances of the detrimental bacteria listed above is inferior to that measured just before FMT.

The Applicant's data (see the Examples below) confirm that the present invention is particularly useful for preventing and/or reducing treatment-induced inflammation in patients suffering from cancer.

The present invention is also useful for preventing and/or reducing treatment-induced inflammation in patients suffering from an hematologic disease, such as an acute leukemia (e.g. acute myeloid leukemia—AML), auto-immune cytopenia and idiopathic bone marrow aplasia.

Furthermore, the Applicant's data in the Examples below reveal the potential of microbiotherapy in the combination with other treatments against blood diseases, especially malignant ones.

Specifically, treatment with FMT product is associated with a decrease inflammatory state in patients (Example 1) in contrast to patients who are not treated with FMT (Example 2). Inflammation and inflammatory syndrome are related to increased co-morbidities and negative scoring of patients. Indeed, blood inflammatory markers such as CRP and serum ferritin have predictive value for the incidence of systemic infection in patients who underwent HSCT (Hong et al., 2015). Interestingly, pre-treatment (i.e. before HSCT conditioning) CRP is a predictor for allo-HSCT outcomes: higher CRP levels are correlated with more grade 3 to 4 infectious toxicity, hepatic toxicity, longer HCT hospital stay, more aGVHD, greater non-relapse mortality and inferior overall survival (Artz et al., 2008). Thus, according to one embodiment of the invention, repeated FMT during leukemic patient's care during the chemotherapeutic courses reduces the inflammatory status and CRP levels thus preventing allo-HSCT toxicities and associated morbidity/mortality (in those patients who are candidates for allo-HSCT). Moreover, the positive impact on local intestinal inflammation has a beneficial effect on patient's quality of life, for example, with the reduction of gastrointestinal disorders, such as abdominal pain and/or diarrhea.

By contrast, the inventor's data in Example 2 show the detrimental impact of a long term antibiotherapy treatment, demonstrated in the OSIRIS protocol with 96 gastro-intestinal related AEs reported in patients that were followed. These patients did not receive FMT. Such a result highlights the need of a combinatory treatment to reduce gut-related inflammation and related complications.

It has been recently shown that gut microbiota can modulate the response to cancer therapy (chemotherapy, radiotherapy and immunotherapy) and susceptibility to toxic side effects (Roy and Trinchieri, 2017; Routy et al., 2018). Restoration of the gut microbiota with an increase of diversity is thus suggested to improve efficacy and reduce the toxicity (Alexander et al., 2017). Moreover, the high diversity of the gut microbiota has been shown to play a key role in overall survival after allo-HSCT and in GvHD patient outcome (Taur et al., 2014). Altogether, these arguments evidence the beneficial impact of a "healthy" and diverse microbiota on the outcomes of patients with cancer and especially hematologic malignancies and strongly support the rationale for using microbiotherapy as adjuvant therapy during all patient's care.

The proportions of beneficial and detrimental bacteria in the microbiota of ODYSSEE patients were clearly modified after IC, with significant decrease of beneficial and increase of detrimental respectively, correlating with increased inflammatory markers assessed in blood and faeces. Indeed, among beneficial bacteria, the inventors have found a specific group of 15 exceptionally beneficial bacterial genus: *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*. The inventors have named this set of genera "butycore".

As described in Example 1, the inventors have correlated the presence of the above 15 genera with a decrease in gut inflammation as evidenced by levels of inflammation markers (fecal and plasmatic) neopterin and plasmatic CRP in the patients. Therefore, the presence of these 15 genera in a fecal sample to be administered in FMT is desirable to maximize the anti-inflammatory capacity of said sample.

Thus, the invention includes administration of fecal microbiota samples in which some or all of the latter 15 beneficial genera, are present.

Among detrimental bacteria, some families comprising pro-inflammatory bacteria such as *Escherichia* or *Klebsiella* were identified. Some of these pro-inflammatory bacteria can be multi-drug resistant such as *Enterococcus* (Steck et al., 2011; Strickertsson et al., 2013), reinforcing the rational to reduce the carriage of these microbes in patients. Noteworthy, 32% of patients in the OSIRIS protocol presented a fecal acquisition of multi-drug resistant bacteria after their antibiotic course (data not shown). Restoration of diversity and of the ratio beneficial/detrimental bacteria after FMT is associated with a reduction of inflammation locally and systemically in the ODYSSEE study, highlighting the potential beneficial anti-inflammatory effect of FMT on the host.

Thus, according to one embodiment of the invention, administration of the fecal microbiota composition to a patient increases the relative abundance of the above mentioned 15 genera and/or a decrease in the abundance of the detrimental pro-inflammatory bacteria.

In particular, according to a preferred embodiment of the invention, the fecal microbiota composition comprises *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*.

Generally, and as shown above, from a therapeutic point of view, the presence of these 15 genera in the fecal microbiota composition is advantageous in the treatment of intestinal inflammation, especially that associated with intestinal dysbiosis.

Providing cancer patients with a fecal microbiota composition generally may regulate gut inflammation and better potentiate other anti-cancer treatments.

The described FMT product herein offers a broad range of activities that create a specific and positive interactive loop between the gut microbiota, the gut metabolism, the gut epithelium and the systemic circulation. Therefore, this positive loop is a crucial step in the immune process to fight cancer cells, especially blood cancer cells, such as myeloid blasts present in AML patients.

Generally, the dysbiosis-induced consequences such as infections and gastrointestinal symptoms such as colitis, diarrhea, abdominal pain, bloating are reduced by administration of the fecal microbiota composition. Preferably, the fecal microbiota composition to be administered to the patient contains some, or more preferably, all of the butyrate producing bacterial genera mentioned above. According to a preferred embodiment of the invention, the fecal microbiota composition to be administered to the patient, comes from at least one, or at least two, or at least three or at least four fecal samples from the same patient. For example, according to one embodiment of the invention, the FMT sample is prepared according to the steps:
 (i) collecting a stool sample and putting it in anaerobic conditions at most 5 minutes after collection;
 (ii) still in anaerobic conditions, mixing the sample with an aqueous saline solution comprising at least a cryoprotectant and/or a bulking agent; and
 (iii) filtering the diluted sample, for example at around 265 µm.
 (iv) pooling several products of step (iii): mixing two or more of said products and homogeneizing the mixture;

Thus, the patient may receive a microbiota composition derived from at leat two pooled fecal inocula (i.e., products of step (iii)). For example, the patient can donate one or more stool samples on one or two or three consecutive days before the anticancer therapy is to take place. These stool samples are used to prepare inocula (product of step iii) which are then pooled (step (iv) above) and then administered as one or two (or more) homogeneous FMT products following the anticancer therapy (e.g., chemotherapy or immunotherapy). If one or more further anti-cancer therapy administrations are envisaged, the next stool samples may be collected once the intestinal microbiota has been sufficiently restored in the individual, usually from about one week (or less if the microbiota bas been restored before then) after the previous FMT treatment. The procedure may thus be repeated as often as necessary, and as long as anti-cancer therapies are carried out.

According to certain embodiments of the invention, the stool samples may be collected from healthy donor (that are not the patient). In this case an allogenic FMT is carried out instead of autologous FMT. In this case, the donors, are screened so that the donor samples are suitable for use in the treatment of a patient, for example, that the samples are free from pathogenic bacteria or viruses. In the case of allogenic FMT, fecal inocula (i.e., products of step (iii), from different donors, may be pooled as described above. Thus, for allogenic FMT samples from one or two, or three or four or more donors may be used. Preferably at least four donors are used, if a pooled allogenic product is used.

The bacterial diversity of the transplanted products is as high as possible and a homogeneity exists between the different doses of products (intra-batch homogeneity) transplanted to the same person. Homogeneity between the different batches produced (inter-batch homogeneity) also exists. The viability of the bacteria is also preserved. The maintainence of high gut microbiota diversity, as demonstrated by the administration of the fecal microbiota compositions described herein has the beneficial effects described above.

The inventors have noted that, in a separate clinical study (ULYSSE, data not shown), the intestinal microbiota composition of 12 patients suffering from AML and who did not receive any FMT, is negatively affected after the first round of an chemotherapy, and remains negatively altered thereafter, having a low microbial species richness and with a microbial composition very different from that of their baseline microbiota (low Bray Curtis similarity).

The data from ULYSSE, which may be viewed as a a sort of negative arm of the ODYSSEE study (but in a different cohort), demonstrates that the anti-inflammatory effect observed in Example 1 is directly due to the administration of the FMT product, as described above.

Other characteristics of the invention will also become apparent in the course of the description which follows of the biological assays which have been performed in the framework of the invention and which provide it with the required experimental support, without limiting its scope.

EXAMPLES

Example 1: Restoration of Gut Microbiota Diversity in Acute Myeloid Leukemia (AML) Patients Undergoing Intensive Chemotherapy with Autologous Fecal Microbiota Transfer (FMT): Results of the Odys Sée Study Patients and Methods
Patients and Study Design
A total of 62 patients aged between 24 and 69 years with a diagnosis of de novo AML were screened from 7 French medical centers between june 2016 and july 2017, and followed until june 2018 (ClinicalTrials Identifier NCT02928523). Patients with acute promyelocytic leukemia, and/or suffering from other severe disease including digestive disorders (inflammatory bowel disease, severe colitis . . . ), or who received antibiotherapy until 4 days before study inclusion were excluded from this trial (Table 1). Bacteriological safety in the feces collected immediately after inclusion was assessed, and detection of MDR bacteria, bacterial pathogens, *Clostridium difficile*, parasites, noroviruses and/or rotaviruses led to the exclusion of the patients. Finally, the treatment cohort comprised 25 patients meeting all the inclusion criteria (Table 2).

and stored as AFMT products in a Good Manufacturing Practices (GMP) platform for future treatment of patients. Patient were then hospitalized for the beginning of IC, and were clinically and biologically monitored according to standard procedures of hematological departments. After hematopoietic recovery, feces and blood were collected within 2 days before antibiotic discontinuation for biochemical, bacteriological, metagenomics and immunological analyses (Visit V2). The AFMT was performed 24 hours after antibiotics discontinuation (at the end of IC and before the start of consolidation chemotherapy), after rectal enema the night before and/or 1 hour before the procedure. Patients received 2 inocula of 150 mL containing 30 g of feces one day apart using a rectal probe introduced in their rectum and were monitored during all the time of transplantation process and until the hospital discharge. Prior to the initiation of consolidation chemotherapy, feces and blood were collected for the same analyses as before (Visit V3), and at the end of the hospitalization, a last feces sample was collected (Visit V4). Quality of life of patients was assessed at each visit (V1

TABLE 1

Selection of patients for the study

| | |
|---|---|
| Inclusion criteria | Patients ≥18 and ≤75 years old with de novo diagnosis of AML or HR MDS for whom intensive induction chemotherapy is anticipated within 10 days after admission; Patients willing to donate stool samples and to follow protocol recommendations; Signature of informed and written consent. |
| Exclusion criteria | Acute promyelocytic leukemia; Known allergy or intolerance to trehalose or maltodextrin; Pregnancy (positive urinary or blood test in female of childbearing potential); Severe disease with a life expectancy <3 months; Other on-going interventional protocol that might interfere with the study; Non eligibility for collection of autologous stools upon admission: Patients refusing to consent; Antibiotherapy at the time of study inclusion ≥4 days; Concomitant or previous diagnosis of a significant inflammatory bowel disease (UC, CD) or other progressive digestive disease requesting treatment or further medical exploration; Presence of severe colitis of any etiology at the time of admission or severe digestive disorders (acute or chronic diarrhea) within 3 months preceding inclusion; Presence of blood in faeces collected at the time of inclusion; Patient getting a recent colonoscopy (within 3 months preceding inclusion); Detection of MDRB, pathogenic bacteria, parasites, norovirus and/or rotavirus during screening of autologous stool collected immediately after the inclusion visit; Non eligibility for inoculum transplantation: persistent mucositis, colitis, or haemorrhoids, presence of blood in more than 1 patient's faeces out of 3 the week preceding the transplantation; Non feasibility of inoculum procedure: patient refusal, technical or biological mismatch of the inoculum; Absence of effective contraceptive method for female of childbearing potential; Lactation; Inability to give an informed consent. |

TABLE 2

Reasons for screening failure (n = 37)

| | |
|---|---|
| Related to IMP manufacturing n = 22 (35%) | Insufficient raw material; n = 14 (23%) Logistic failure; n = 4 (6%) Quality control for batch release not reached; n = 4 (6%) |
| Related to the patient n = 15 (24%) | FMT not performed due to patient condition; n = 6 (10%) Consent withdrawal; n = 2 (3%) AML diagnosis not confirmed; n = 1 (2%) MDRB or *C. difficile* carriage at diagnosis; n = 6 (10%) |

Immediately after inclusion of patients and prior to the initiation of the induction chemotherapy (IC) and any antibiotherapy, feces and blood were collected (Visit V1, day 0) (see FIG. 1 for study flowchart). Bacteriological, biochemical and metagenomic analyses were performed on feces samples, and immunological and biochemical analyses were performed on plasma samples. The feces were manufactured to V4), using an EQ-5D-5L questionnaire evaluating the mobility, self-care, usual activities, pain/discomfort, anxiety and depression. Finally, after 6 months (Visit V5) and 1 year (Visit V6), clinical information and safety assessment were reported.

Among the 25 treated patients, 4 patients received AFMT after the first consolidation chemotherapy and not before due to patient condition (AFMT was not feasible because of colitis or hemorrhoids) and one protocol deviation was observed in one patient: 20 patients were thus considered as per protocol. All Figures and Tables will present the data obtained from these patients except when otherwise specified.

Production of AFMT Inocula

Feces were collected at the time of patient's admission, before the beginning of IC. Feces were processed within 72 h with a cryoprotective diluent as described in WO 2016/170285 (A1) and WO 2017/103550 (A1) into a proprietary device (similar to that described in WO 2016/170290 (A1)) under GMP conditions, filtered, conditioned, and stored frozen at −80° C. until transplantation. More precisely, a first visual check ensured the absence of urine and blood, and the assessment of the texture based on Bristol stool scale. Then the feces were weighed to adapt the quantity of cryoprotective diluent to be used. Diluent was then added in the device, and a gentle mixing of both ensured the homogenization of the suspension. The suspension is filtered at the same time as the mixing makes it go through the sieve. All these steps are performed in the hermetically closed device, ensuring that no air is in contact with the microbiota. The suspension is then collected via the bottom port of the device and conditioned via closed systems and tubings in a cryo-resistant plastic bag, displaying several connections, to allow entering and exiting of the product by separate ways. Samples are collected at the end of this step to be used as QC. The product is finally stored at −80° C. Microbiological testings (performed on the fresh stools according to Health Agency guideline), and viability assessment by flow cytometry are finally performed prior the release of the product.

In parallel, rigorous microbiological screening was performed (see Microbiological analyses section and Table 3) and allowed the release of the Investigational Medicinal Product (IMP) after a quarantine period.

TABLE 3

List of screening tests performed in faeces for batch release

| Microbiology (feces) | C. difficile | | PCR |
|---|---|---|---|
| | Norovirus | | PCR |
| | Rotavirus | | Immunochromatography |
| | MDRB | MRSA | PCR |
| | | VRE et GRE | Culture (2 specific media) |
| | | ESBLs | Culture (2 specific media) |
| | | Carbapenemases | Culture (2 specific media) |
| Pathogenic bacteria | Campylobacter sp | | PCR |
| | Listeria sp | | Culture (ALOA) |
| | Salmonella sp | | PCR |
| | Shigella sp | | PCR |
| | Vibrio sp | | Culture (after enrichment) |
| | Yersinia sp | | Culture (Cefsulodin-Irgasan-Novobiocine) |
| Parasites | Strongyloides stercoralis, Cyclospora, Isospora, Entamoeba histolytica, Giardia intestinalis, Cryptosporidium, | | Faeces concentration - coproculture and PCR |

TABLE 3-continued

List of screening tests performed in faeces for batch release

Microsporidies,
Dientamoeba fragilis,
Blastocystis hominis

Microbiological Analyses

Detection of C. difficile, Salmonella sp., Shigella sp., and MDR bacteria (methicillin resistant Staphylococcus aureus, vancomycin- and glycopeptide-resistant Enterococci, extended-spectrum beta-lactamase (ESBL) producing bacteria and carbapenemase-producing bacteria) was performed in feces samples collected during the first three visits using PCR and culture on specific isolation media respectively. Parasites, viruses and pathogenic bacteria were screened in the feces samples collected during the first visit to verify the safety of feces for AFMT use. Parasites were detected using PCR (Microsporidia, Dientamoeba fragilis) or microscopy (Strongyloides stercoralis, Cyclospora sp., Isospora sp., Entamoeba histolytica, Giardia intestinalis, Cryptosporidium sp., Blastocystis hominis) after feces concentration. Noroviruses and Rotaviruses were identified by PCR and immunochromatography respectively, and pathogenic bacteria were detected using PCR (Campylobacter) and culture (Listeria sp., Vibrio sp., Yersinia sp.).

Biochemical and Immunological Analyses

Biochemical and immunological analyses were performed on the different blood and feces samples collected during the first three visits. Neopterin and secretory IgA (sIgA) were measured from feces supernatants using the Neopterin ELISA (IBL International) and IgA Secretory Human ELISA (EUROBIO) kits respectively. Total Antioxidant Status (TAS) was measured from plasma using the Hitachi 912 kit (RANDOX Laboratories), CRP and ferritin were measured from plasma/serum samples in the different medical centers according to their own internal procedures. Immunological markers were measured from plasma samples: IL6 and TNFα (Human Cytokine/Chemokine Magnetic Bead Panel kit (EMD Millipore)); soluble CD14 (sCD14) (Human CD14 Quantikine ELISA kit (R&D System).

DNA Isolation and Metagenomic Sequencing

Genomic DNA was extracted from the feces samples collected during the first four visits using the NucleoSpin Soil kit (Macherey Nagel). A sequencing library was constructed for each DNA sample using the TruSeq kit (Illumina) according to the manufacturer's instructions. Libraries were then sequenced in 2 paired-end (2×125 bp) HiSeq2500 (Illumina) runs.

Bioinformatics Analyses

After quality filtering using Trimmomatic (Bolger, Lohse and Usadel, 2014), host sequence decontamination was performed using Bowtie2 (Langmead, Ben and Salzberg, 2013). Thus, between 936060 and 37212124 pairs of reads (mean: 34811750 pairs of reads) were obtained from the different samples. For fair comparison, the sequence number of each sample was randomly normalized to the same sequencing depth i.e. 1500000 paired-end sequences per sample. Taxonomic profiling was then performed with Kraken v.0.10.5-beta (Wood 2014) and the RefSeq genomic database (June 2015 release, world wide web at ncbi.nlm-.nih.gov/refseq/). The measure of median α- and β diversity indexes was performed in R Statistical Software after 10 subsamplings (R Core Team 2015, version 3.4.4, world wide web at R-project.org) using vegan and phyloseq packages. The proportion of beneficial bacteria was defined as the sum of relative abundances (based on microbiota taxonomic profiling) of beneficial microbial families: Lachnospiraceae, Ruminococcaceae, Bifidobacteriaceae, Streptococcaceae, Akkermansiaceae, Lactobacillaceae, Eubacteriaceae, Erysipelotrichaceae, Eggerthellaceae, Clostridiaceae, Prevotellaceae and Oscillospiraceae. Similarly, the proportion of detrimental bacteria was defined as the sum of abundances of Bacteroidaceae and Enterococcaceae families.

Gene-based and antibioresistance analyses were performed through gene mapping with Bowtie 2 using the Integrated Gene Catalogue (IGC) (Li et al., 2014) and MEGARes (world wide web at megares.meglab.org/) databases respectively.

Statistical Analyses

Ratios of V3/V1 and V2/V1 of the following parameters have been compared thanks to a bilateral paired-t-test:
Richness Indexes for Species and Genes
Simpson Index for Species
Wilcoxon paired test was applied to the following parameters:
Copy number of antibiotic resistance
Beneficial-Detrimental bacteria (%)
Bray-Curtis index
CRP, Ferritin, Neopterin, IL-6, sCD14, IgA, TNFα, TAS Results Patient Characteristics A total of 62 AML patients were screened in our study in 7 different centers, 25 were treated with AFMT, and 20 were considered as the per-protocol population on which the following analyses have been performed. The baseline characteristics of treated and per protocol patients are listed in Table 4. There were more men than women in the per protocol patient population (ratio, 3:1) and the median age was 50 years. Most patients (80% of both treated and per protocol patients) were considered as being from intermediate-risk AML, while 3 and 2 patients of the treated population were from the favorable and unfavorable risk groups, respectively. All patients received intensive induction chemotherapy (classical "3+7" regimen or equivalent).

second AFMT respectively instead of the recommended 120 min) demonstrating the feasibility of enema procedure and the absence of discomfort for the patients.

During the AFMT treatment, no harmful changes in vital signs of treated patients were observed (heart rate, blood pressure). Then, during the first 24 h after AFMT, 5 adverse events (AEs) were reported in 4 treated patients (16%). (Table 5).

No serious adverse events (SAEs) were reported during this period in the treated population.

TABLE 5

AEs 24-hours after AFMT by SOC in treated patients (n = 25).

| SOC | PT | # (%) |
|---|---|---|
| Gastrointestinal disorders | Abdominal pain | 1 (20%) |
|  | Diarrhea | 2 (40%) |
| General disorders and administration site conditions | Pyrexia | 1 (20%) |
| Investigations | Weight increased | 1 (20%) |

After the first 24 h post AFMT and until the end of the 1-year follow-up period, 415 AEs were reported in 24 of the 25 treated patients (96%) (Table 6). Among them, 2 were related to enema procedure and 1 to the AFMT product. The other AEs were all in line with leukaemia patient profiles. The most common AEs were blood and lymphatic system disorders (n=58; 14%), gastrointestinal disorders (n=78; 19%), general disorders and administration site conditions (n=39; 9%), and infections and infestations (n=88; 21%). Most AE occurred between inclusion and AFMT (V1-V2) (incidence rate of 27.06%) and between visit V3 and visit V4 (incidence rate of 15.07%) (Supplementary Figure S2). In addition, 30 serious adverse events (SAEs) have been reported in 15 patients (15%) (Table 7), most of them being infections and infestations (n=13; 43%). As for AEs, most SAEs occurred between inclusion and AFMT (V1-V2) (incidence rate of 1.57%) and between visit V3 and visit V4 (incidence rate of 0.90%). None of these SAEs occurred during the first month following AFMT, and only one was

TABLE 4

Baseline demographics and clinical characteristics of treated and per protocol patients.

|  |  | Treated patients (n = 25) |  | Per protocol patients (n = 20) |  |
|---|---|---|---|---|---|
|  |  | # | % | # | % |
| Gender | Male | 18 | 72.00 | 15 | 75.00 |
|  | Female | 7 | 28.00 | 5 | 25.00 |
|  | Missing data | 0 | 0.00 | 0 | 0.00 |
| Age at inclusion (years) | Mean | 50.68 | — | 49.05 | — |
|  | Median | 52 | — | 50 | — |
|  | Range | [24-68] | — | [24-68] | — |
|  | Missing data | 0 | — | 0 | — |
| Risk category | Favourable | 3 | 12.00 | 2 | 10.00 |
|  | Intermediate | 20 | 80.00 | 16 | 80.00 |
|  | Unfavourable | 2 | 8.00 | 2 | 10.00 |
|  | Missing data | 0 | 0.00 | 0 | 0.00 |
| BMI at inclusion | Mean | 27.44 | — | 28.32 | — |
|  | Median | 26.33 | — | 26.54 | — |
|  | Range | [19, 72-41, 34] | — | [21.24-41.34] | — |
|  | Missing data | 0 | — | 0 | — |

BMI: Body Mass Index

Safety Results

Mean AFMT product retention time was longer than expected (189.50 min and 173.33 min for the first and declared to be possibly related to the AFMT treatment by the site investigator. The patient exhibited hyperthermia and gastrointestinal symptoms 93 days after the second AFMT and was diagnosed with *Escherichia coli* sepsis. The subject's past medical history included colonization by multi-drug resistant *E. coli* in the faeces after hospitalization for consolidation chemotherapy, i.e. 22 days after the second AFMT. After antibiotherapy, the patient fully recovered. This multi-drug resistant bacterium was not detected in faeces collected at the beginning of the consolidation chemotherapy. This SAE occurred 3 months after AFMT, which thus raises the question of its link to the administered treatment.

TABLE 6

AEs after the first 24-hours after AFTM by SOC in treated patients (n = 25).

| SOC | # (%) |
|---|---|
| Blood and lymphatic system disorders | 58 (14%) |
| Cardiac disorders | 2 (0%) |
| Congenital, familial and genetic disorders | 8 (2%) |
| Eye disorders | 1 (0%) |
| Gastrointestinal disorders | 78 (18%) |
| General disorders and administration site conditions | 39 (9%) |
| Hepatobiliary disorders | 8 (9%) |
| Immune system disorders | 6 (1%) |
| Infections and infestations | 88 (21%) |
| Injury, poisoning and procedural complications | 13 (3%) |
| Investigations | 20 (5%) |
| Metabolism and nutrition disorders | 14 (3%) |
| Musculoskeletal and connective tissue disorders | 12 (3%) |
| Nervous system disorders | 18 (4%) |
| Psychiatric disorders | 5 (1%) |
| Renal and urinary disorders | 2 (0%) |
| Reproductive system and breast disorders | 1 (0%) |
| Respiratory, thoracic and mediastinal disorders | 17 (4%) |
| Skin and subcutaneous tissue disorders | 15 (4%) |
| Surgical and medical procedures | 1 (0%) |
| Vascular disorders | 9 (2%) |

TABLE 7

SAEs after the first 24-hours after AFMT by SOC in treated patients (n = 25).

| SOC | # (%) |
|---|---|
| Blood and lymphatic system disorders | 1 (3%) |
| Gastrointestinal disorders | 1 (3%) |
| General disorders and administration site conditions | 3 (10%) |
| Immune system disorders | 3 (10%) |
| Infections and infestations | 13 (43%) |
| Injury, poisoning and procedural complications | 2 (6%) |
| Investigations | 1 (3%) |
| Metabolism and nutrition disorders | 1 (3%) |
| Nervous system disorders | 1 (3%) |

TABLE 7-continued

SAEs after the first 24-hours after AFMT by SOC in treated patients (n = 25).

| SOC | # (%) |
|---|---|
| Respiratory, thoracic and mediastinal disorders | 2 (6%) |
| Skin and subcutaneous tissue disorders | 1 (3%) |
| Vascular disorders | 1 (3%) |

Four deaths were reported among the 25 treated patients (16%) (same results in the per protocol population: 4 deaths among 20 patients (20%)) (Table 8). The median time to death from the second AFMT was 182.5 days (range: 113-225 days). One patient died of multiple organ failure 34 days after HSCT (143 days after AFMT). Another patient experienced multiple organ failure in a context of infections during post-allograft aplasia (113 days after AFMT). A heart attack after pulmonary embolism, possibly related to medical history of chronic atrial fibrillation and arterial hypertension, was reported. The death occurred 225 days after AFMT. The fourth death (222 days after AFMT) was due to grade IV resistant gastro-intestinal GvHD, aggravated by septicaemia to ESBL-producing *Klebsiella pneumoniae* and *Stenotrophomonas maltophilia*, the presence of multiresistant *Enterobacter cloacae* in the urines, cytomegalovirus reactivation, human herpes virus 6 viremia and a context of acute encephalitis. All deaths were considered by the site investigator and confirmed by the Data and Safety Monitoring Board (DMSB) to be unrelated to AFMT treatment.

TABLE 8

Clinical outcomes of treated patients (n = 25).

| | 6 months | 12 months |
|---|---|---|
| Complete remission | 21 (84%) | 17 (68%) |
| Partial remission | 1 (4%) | 1 (4%) |
| Progression | 0 (0%) | 3 (12%) |
| Death | 3 (12%) | 4 (16%) |

Per protocol patient quality of life was evaluated throughout the clinical study. Data obtained showed that the results of the questionnaire after AFMT (V3) were similar or tended to improve compared to those at V2 before AFMT (especially self-care, usual activities and anxiety and depression parameters), which highlights the absence of negative impact of AFMT on the overall health of patients (Table 9). Similarly, no significant BMI variation was observed throughout the study for treated patients, but the mean weight tended to increase between V2 and V3 (26.89 to 27.26) suggesting the absence of digestive problems in treated patients.

TABLE 9

Descriptive statistics of quality of life questionnaire for treated patients

| Parameters | Statistics | D0 | D29 | D40 | D70 |
|---|---|---|---|---|---|
| Mobility | Missing | 3 | 4 | 6 | 7 |
| | I have no problems in walking about | 18 (81.82%) | 18 (85.71%) | 16 (84.21%) | 14 (77.78%) |
| | I have slight problems in walking about | 3 (13.64%) | 3 (14.29%) | 3 (15.79%) | 3 (16.67%) |
| | I have moderate problems in walking about | 1 (4.55%) | 0 (0.00%) | 0 (0.00%) | 1 (5.56%) |

TABLE 9-continued

Descriptive statistics of quality of life questionnaire for treated patients

| Parameters | Statistics | D0 | D29 | D40 | D70 |
|---|---|---|---|---|---|
| | I have severe problems in walking about | 0 (0.00%) | 0 (0.00%) | 0 (0.00%) | 0 (0.00%) |
| | I am unable to walk about | 0 (0.00%) | 0 (0.00%) | 0 (0.00%) | 0 (0.00%) |
| Self-care | Missing | 3 | 4 | 5 | 7 |
| | I have no problem washing or dressing myself | 21 (95.45%) | 19 (90.48%) | 19 (95.00%) | 16 (88.89%) |
| | I have slight problems washing or dressing myself | 1 (4.55%) | 2 (9.52%) | 1 (5.00%) | 2 (11.11%) |
| | I have moderate problems washing or dressing myself | 0 (0.00%) | 0 (0.00%) | 0 (0.00%) | 0 (0.00%) |
| | I have severe problems washing or dressing myself | 0 (0.00%) | 0 (0.00%) | 0 (0.00%) | 0 (0.00%) |
| | I am unable wash or dress myself | 0 (0.00%) | 0 (0.00%) | 0 (0.00%) | 0 (0.00%) |
| Usual activities | Missing | 5 | 4 | 5 | 7 |
| | I have no problems doing my usual activities | 12 (60.00%) | 13 (61.90%) | 15 (75.00%) | 11 (61.11%) |
| | I have slight problems doing my usual activities | 4 (20.00%) | 6 (28.57%) | 4 (20.00%) | 5 (27.78%) |
| | I have moderate problems doing my usual activities | 2 (10.00%) | 2 (9.52%) | 1 (5.00%) | 2 (11.11%) |
| | I have severe problems doing my usual activities | 1 (5.00%) | 0 (0.00%) | 0 (0.00%) | 0 (0.00%) |
| | I am unable do my usual activities | 1 (5.00%) | 0 (0.00%) | 0 (0.00%) | 0 (0.00%) |
| Pain/Discomfort | Missing | 3 | 4 | 5 | 7 |
| | I have no pain or discomfort | 10 (45.45%) | 17 (80.95%) | 16 (80.00%) | 13 (72.22%) |
| | I have slight pain or discomfort | 8 (36.36%) | 4 (19.05%) | 4 (20.00%) | 4 (22.22%) |
| | I have moderate pain or discomfort | 4 (18.18%) | 0 (0.00%) | 0 (0.00%) | 1 (5.56%) |
| | I have severe pain or discomfort | 0 (0.00%) | 0 (0.00%) | 0 (0.00%) | 0 (0.00%) |
| | I have extreme pain or discomfort | 0 (0.00%) | 0 (0.00%) | 0 (0.00%) | 0 (0.00%) |
| Anxiety and depression | Missing | 3 | 4 | 5 | 8 |
| | I am not anxious or depressed | 11 (50.00%) | 14 (66.67%) | 15 (75.00%) | 8 (47.06%) |
| | I am slight anxious or depressed | 5 (22.73%) | 4 (19.05%) | 3 (15.00%) | 6 (35.29%) |
| | I am moderately anxious or depressed | 4 (18.18%) | 3 (14.29%) | 2 (10.00%) | 3 (17.65%) |
| | I am severely anxious or depressed | 2 (9.09%) | 0 (0.00%) | 0 (0.00%) | 0 (0.00%) |
| | I am extremely anxious or depressed | 0 (0.00%) | 0 (0.00%) | 0 (0.00%) | 0 (0.00%) |
| Your health today | N (Missing) | 20 (5) | 21 (4) | 20 (5) | 17 (8) |
| | Mean (SD) | 61.05 (26.05) | 76.24 (16.44) | 78.75 (16.61) | 71.47 (15.49) |
| | (Min; Max) | (9.00; 95.00) | (45.00; 100.00) | (50.00; 95.00) | (40.00; 95.00) |
| | Median (Q1; Q3) | 62.50 (47.50; 80.00) | 80.00 (70.00; 90.00) | 85.00 (65.00; 95.00) | 70.00 (65.00; 80.00) |

The safety of AFMT was evaluated by the measurement of inflammatory parameters both locally in the gut and systematically in the plasma during the 3 first visits. In a systemic approach, we measured inflammatory proteins and cytokines in plasma such as C-Reactive Protein (CRP), ferritin, IL-6, TNFα and sCD14 (FIGS. 2 and 3). We observed a significant increase of CRP at V2 (V1: 11.80±18.25 mg/L; V2: 24.40±23.92 mg/L; p=0.04) and a return to baseline at V3 (V3: 10.16±22.07 mg/L; V2 vs V3: p=0.02). Ferritin levels followed the same variations with an increase at V2 and a return to baseline at V3. Additional trends were observed with quantification of other inflammatory parameters showing no significant increase of IL-6, TNFα and sCD14 after AFMT treatment (FIG. 3). We also measured the Total Antioxidant Status (TAS) in plasma as a marker of oxidative stress that can be induced by gut microbiota alterations. Previous studies have reported that oxidative stress is closely related to the occurrence and development of cancers (Wu et al., 2017) and is also associated with gut dysbiosis. Oxidative stress occurring during inflammation is a factor amplifying dysbiosis by strongly decreasing the microbial diversity in the gut and by promoting the outgrowth of specific bacterial taxa (Weiss and Hennet, 2017). We observed a decrease of TAS levels between V1 and V2 (V1: 1.33±0.09 mmol/L; V2: 1.31±0.19 mmol/L) and a significant increase after AFMT (V3: 1.59±0.58 mmol/L; p=0.006) that could be associated with gut microbiota restoration.

The local immunity and inflammation in the gut was assessed by measuring fecal neopterin and secretory IgA. Neopterin is produced and released from activated macrophages stimulated with various inducers such as IFNγ, TNFα and bacterial components (Nancey et al., 2013) and reflects the degree of cell-mediated immune response and thereby the levels of intestinal inflammation. We observed a significant increase of mean fecal neopterin levels after IC (V1: 2.79±4.02 ng/g of feces versus V2: 32.70±40.15 ng/g of feces; p=0.0006) highlighting the expected inflammatory intestinal status of patients after IC and antibiotherapy. Levels were significantly decreased and returned to baseline following AFMT (V3: 5.41±7.42 ng/g of feces; p=0.001). These variations are in line with CRP variations. As a mirror of local immunity, secretory IgA were also measured in feces and similar trends were observed (V1: 1.95±2.05 mg/g of feces; V2: 2.75±1.81 mg/g of feces; V3: 2.39±2.15 mg/g of feces). Altogether, these data clearly point out to the absence of any deleterious inflammatory reaction, both locally and systematically after AFMT.

Evolution of the Gut Microbiota Composition

The impact of IC and subsequent AFMT treatment on the phylogenetic richness and diversity of fecal microbiota in per protocol patients was then examined. The inventors demonstrated that IC induces a dramatic shift in microbial communities, with a statistically significant decrease of α-diversity indexes between V1 and V2 at the species level: 39.3% estimated reduction in mean richness (960.45 to 589.71 species; p<0.001) (FIG. 4a) and 42.3% estimated reduction in mean Simpson index (0.85 to 0.50; p<0.001) (FIG. 4b and FIG. 5). After AFMT treatment, species richness (957.70 species; p<0.001) and Simpson index (0.86; p<0.001) returned to their initial level with no statistical difference between values at V1 and V3. Thus, the gut microbiota at V3 after AFMT is reconstructed to more than 90% in the per protocol population based on both richness and Simpson index at the species level (p<0.001). This modification of microbial communities is also observed with measures of β-diversity (FIG. 4c and FIG. 5). Indeed, the Bray-Curtis dissimilarity index (BC) demonstrates the induction of a microbial dysbiosis after IC (mean BC V1-V2: 0.76) and the restoration of microbial communities after AFMT treatment whose composition is closer to that of the initial communities at the species level (mean BC V1-V3: 0.40). (FIG. 5).

The proportion of beneficial and detrimental bacteria in the microbiota of per protocol patients between V1 and V3 (FIGS. 5a and 5b) was then measured. The proportion of beneficial bacteria was significantly reduced between V1 and V2 (mean V1: 5.54%; V2: 2.43%; p<0.01) and was then increased to return to its baseline level at V3 after AFMT (mean V3: 6.82%). On the contrary, the proportion of detrimental bacteria significantly increased at V2 (mean V1: 10.95%; V2: 32.29%; p<0.5) and decreased to return to its initial status at V3 after AFMT (mean V3: 10.65%).

In order to evaluate the functional richness of gut microbiota over the course of treatment, the total number of genes in the gut microbiota of per protocol patients was evaluated through mapping of reads against the IGC database. Results demonstrate that the mean number of genes is significantly reduced by 78% (531500.20 to 21361.50 total genes; p<0.001) after IC and significantly increased after AFMT (424374.15 genes) so that more than 70% of the initial gene richness is recovered for the per protocol population (p=0.025) (FIG. 4d, FIG. 5).

Determination of a Refined List of Butyric Acid Producers, Associated with Decreased Inflammation Based on the Clinical Data:

Based on a list of 34 butyrate producing genera built from literature, the inventors performed a correlation test between the level of each genus and fecal neopterin (inflammation marker) in patients in the ODYSSEE trial to determine a refined list of butyrate producers, (called butycore). Spearman correlations and Spearman correlation tests were computed with R (function correlation test from statistics package). No multiple test correction was applied for these analyses.

Results:

A list of 15 butyrate producing genera that are significantly correlated with fecal neopterin and have an estimated relative abundance >0.1% in the ODYSSEE study was determined. This list is composed of *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio* genera (see Table 10).

TABLE 10

Fifteen butyrate producing genera based on correlation analysis and relative abundance filtering.

| Butyrate producers (literature) | Odyssee Spearman correlation | Odyssee cortest pvalue | Odyssee prevalence (V1) | Odyssee average RA (V1) |
|---|---|---|---|---|
| Blautia | −0.50 | 1.54E−05 | 100.00 | 5.39 |
| Faecalibacterium | −0.54 | 2.02E−06 | 100.00 | 5.28 |
| Alistipes | −0.47 | 6.06E−05 | 100.00 | 4.75 |
| Eubacterium | −0.66 | 1.05E−09 | 100.00 | 1.54 |
| Bifidobacterium | −0.48 | 3.41E−05 | 92.00 | 1.24 |
| Ruminococcus | −0.68 | 2.47E−10 | 100.00 | 1.13 |
| Clostridium | −0.61 | 4.58E−08 | 100.00 | 0.95 |
| Coprococcus | −0.59 | 1.42E−07 | 100.00 | 0.86 |
| Odoribacter | −0.53 | 3.11E−06 | 100.00 | 0.63 |
| Roseburia | −0.64 | 6.44E−09 | 100.00 | 0.56 |
| Holdemanella | −0.56 | 7.90E−07 | 80.00 | 0.34 |
| Anaerostipes | −0.51 | 1.04E−05 | 96.00 | 0.25 |
| Oscillibacter | −0.60 | 6.19E−08 | 100.00 | 0.21 |
| Subdoligranulum | −0.56 | 7.04E−07 | 100.00 | 0.17 |
| Butyrivibrio | −0.59 | 1.13E−07 | 88.00 | 0.14 |

In the ODYSSEE trial, the 15 butyrate producing genera negatively correlate with fecal and plasmatic neopterin and CRP. Relative abundance decreases at V2 after chemotherapy and IC, and is restored to baseline at V3 after aFMT treatment. For most of patients, the majority of the 15 genera are present at V1 (baseline), most genera are eliminated at V2, and restored due to the FMT at V3 which shows a butycore similar to the one measured at V1 (FIG. 6).

MDRB Decolonization

The presence of *C. difficile* and MDRB in feces of patients was evaluated between V1 and V3 by analysis of resistance genes in the metagenomic dataset.

The total sequencing reads were mapped on the MEGARes antibioresistance gene database. It was seen that IC and associated antibiotic treatments induced a significant increase in the mean number of reads mapped against antibioresistance genes at V2 (167546 to 371465 reads, p<0.01) for per protocol patients. Then, a significant reduction of 43% of the mean number of reads mapped was observed at V3 after AFMT (211127 reads, p<0.001).

Clinical Outcomes

Clinical outcomes are summarized in Table 2. Median follow-up time for dead patients was 7.13 months (range, 4.8-8.5 months). At 6 months, the overall survival (OS) rate was 88% (3 deaths) (FIG. 8). Among the treated patients, 21 (84%) achieved complete remission based on haematological response, and 1 (4%) achieved partial remission. The 1-year OS rate was 84% (4 deaths) for the treated population (FIG. 8). A total of 17 patients (68%) were still in complete remission at 12 months, and 1 patient (4%) was in partial remission. In addition, a leukemia progression was observed for 3 (12%) of the treated patients at one year.

Example 2: Results of the Osiris Clinical Study Showing that Iatrogenic Dysbiosis and Gut Inflammation does not Normalize in the Absence of FMT Patients and Methods
Patients and Study Design A total of 62 patients with suspicion of Bone and Joint infection (BJI) were screened from 5 French medical centers between January 2017 and September 2017 and followed until march 2018 (ClinicalTrials Identifier NCT03011502). Patients were classified in 3 categories as follow: native (n=27, mean of age=56), osteosynthesis (n=13, mean of age=52) and prosthesis (n=22, mean of age=66) BJI.

TABLE 11

Selection of patients for the OSIRIS study

| | |
|---|---|
| Inclusion criteria | The subject is willing, able to understand and comply to the protocol requirement<br>More than 18-years-old<br>Subject is suspected for implanted or native BJI and is eligible for antibiotics treatment<br>Subject signed Inform Consent Form |
| Exclusion criteria | Pregnancy<br>Severe disease with a life expectancy <3 months<br>Any Antibiotherapy in the 14 days before inclusion<br>Guardianship, curatorship patients<br>Patient non-affiliated to health care system<br>Patient under the power of law |

Immediately after inclusion of patients and prior to the initiation of the antibiotherapy, feces and blood were collected (Visit V1, day 0) (see FIG. 8 for study flowchart). Bacteriological, biochemical and metagenomic analyses were performed on feces samples, and biochemical analyses were performed on plasma samples. After antibiotherapy completion, feces and blood were collected for biochemical, bacteriological, metagenomics analyses (Visit V3). Two weeks after the antibiotherapy discontinuation, feces and blood were collected for the same analyses as before (Visit V4). Quality of life of patients was assessed at each visit (V1 to V4), using an EQ-5D-5L questionnaire (evaluating the mobility, self-care, usual activities, pain/discomfort, anxiety and depression). Finally, after 6 months post inclusion (Visit V5), clinical information and safety assessment were reported.

Microbiological Analyses

Detection of C. difficile, Salmonella sp., Shigella sp., and MDR bacteria (methicillin resistant Staphylococcus aureus, vancomycin- and glycopeptide-resistant Enterococci, extended-spectrum beta-lactamase (ESBL) producing bacteria and carbapenemase-producing bacteria) was performed in feces samples collected during the five visits using PCR and culture on specific isolation media respectively.

Biochemical Analyses

Biochemical analyses were performed on feces samples collected during visits V1, V3 and V4. Neopterin and secretory IgA (sIgA) were measured from feces supernatants using the Neopterin ELISA (IBL International) and IgA Secretory Human ELISA (EUROBIO) kits respectively. CRP was measured from plasma samples in the different medical centers according to their own internal procedures.

DNA Isolation and Metagenomic Sequencing

Genomic DNA was extracted from the feces samples collected during the first four visits using the NucleoSpin Soil kit (Macherey Nagel). A sequencing library was constructed for each DNA sample using the TruSeq kit (Illumina) according to the manufacturer's instructions. Libraries were then sequenced in 2 paired-end (2×125 bp) HiSeq2500 (Illumina) runs.

Bioinformatics Analyses

After quality filtering using Trimmomatic (Bolger, Lohse and Usadel, 2014), host sequence decontamination was performed using Bowtie2 (Langmead, Ben and Salzberg, 2013). For fair comparison, the sequence number of each sample was randomly normalized to the same sequencing depth i.e. 1500000 paired-end sequences per sample. Taxonomic profiling was then performed with Kraken v.0.10.5-beta (Wood 2014) and the RefSeq genomic database (June 2015 release, world wide web at ncbi.nlm.nih.gov/refseq/). The measure of median $\alpha$- and $\beta$ diversity indexes was performed in R Statistical Software after 10 subsamplings (R Core Team 2015, version 3.4.4, world wide web at R-project.org) using vegan and phyloseq packages. Gene-based and antibioresistance analyses were performed through gene mapping with Bowtie 2 using the Integrated Gene Catalogue (IGC) (Li et al., 2014) and MEGARes (world wide web at megares.meglab.org/) databases respectively.

Statistical Analyses

Paired t tests

Results

Patient Characteristics

A total of 62 BJI patients were screened in our study in 5 different centers, 42 were considered as the intention to treat population on which some analyses have been performed. The baseline characteristics of the total and per protocol patients are listed in Table 12. There were more men than women in per protocol patients (ratio, 2:1) and the median age was 59 years.

TABLE 12

Baseline demographics and clinical characteristics.

| | | Total patients | |
|---|---|---|---|
| | | # | % |
| Sex | Male | 40 | 64.50 |
| | Female | 22 | 35.50 |
| | Missing data | 0 | 0.00 |
| Age at inclusion (years) | Mean | 59 | — |
| BMI at inclusion | Mean | 27.45 | — |
| SOC Antibiotherapy | Gasto-intestinal AEs | 36 (96 AE) | 69.2% |
| | penicillins | — | — |
| | cephalosporins | — | — |
| | aminosides | — | — |
| | quinolones | — | — |

BMI: Body Mass Index

Then the local immunity and inflammation in the gut was assessed, by measuring fecal zonulin, calprotectin, neopterin and secretory IgA. We observed a significant increase of mean fecal neopterin levels after antibiotherapy therapy (V1: 97.7 ng/g of feces versus 504 ng/g of feces after treatment; p<0.001) highlighting the expected inflammatory intestinal status of patients after antibiotherapy. Levels did not return to baseline two weeks after the end of antibiotherapy (285.4 ng/g of feces; p=0.02). These variations are in line with zonulin concentrations.

Altogether, these data clearly point out to the presence of a deleterious inflammatory reaction, locally, after antibiotherapy. Of note, almost 70% of the patients from the OSIRIS protocol, with no FMT treatment, suffered of gastro-intestinal symptoms. 9 of them, out of 42 patients with follow up, presented severe diarrhea symptoms.

Evolution of the Gut Microbiota Composition

The Bray-Curtis (BC) dissimilarity index measured at the species level (data not shown) demonstrates the induction of a microbial dysbiosis after antimicrobial treatment (mean BC V1-V3: 0.321) and the absence of restoration of the initial microbial community after two weeks (mean BC V1-V4: 0.367).

In the OSIRIS study, relative abundance of the 15 butyrate-producing genera discussed above also negatively correlates with fecal neopterin and relative abundance of butycore decreases after antimicrobial treatment.

Example 3: Bacteria Profile of the Stool Sample Used to Produce the Fecal Microbiota Composition is Maintained in Final Product The inocula produced as described in WO 2016/170285 A1 into a proprietary device (similar to that described in WO 2016/170290 A1) allow the excellent conservation of all families and genera of bacteria belonging to the human microbiota collected. Furthermore, the closed process prevents the contamination by other environmental bacteria.

Four fresh stools and inocula produced according to the above described process were analyzed using 16S rDNA analysis. All samples were stored at −80° C. and DNA were extracted using the NUCLEOSPIN® Soil Kit (Macherey Nagel). 16S rDNA Libraries were performed with the MyTag HS Mix kit (Bioline) using primers targeting the V3-V4 region. Sequencing was performed to obtain 80 000-90 000 pairs of reads (160 000-180 000 reads) per library. Sequencing of 16S rDNA libraries was realized using a MiSeq V3 2×300 bp sequencer (Illumina).

The microbiota has been analyzed at all taxonomical levels, and results for main families and genera are presented in Table 13 and Table 14.

These analyses demonstrate that the process allows the conservation of all the bacteria present in the original stools with close relative abundances; usually more than 90% of the genera observed in the initial stools are maintained in the frozen product.

TABLE 13

Relative abundances (in %) of main families identified in 4 stools (identified SF) and corresponding inocula (identified IN)

|  | S322_IN OC | S322E_ SF | S325_IN OC | S325_ SF | S327_IN OC | S327_ SF | S328_IN OC | S328_ SF |
|---|---|---|---|---|---|---|---|---|
| Fusobacteriaceae | 0.01 | 0.01 | 0 | 0 | 0.03 | 0 | 0 | 0 |
| Bacteroidales S24-7 group | 0 | 0 | 0 | 0 | 0 | 0 | 0.08 | 0.01 |
| Defluviitaleaceae | 0.02 | 0.02 | 0.02 | 0.02 | 0.03 | 0.02 | 0 | 0 |
| gut metagenome | 0.03 | 0.01 | 0.02 | 0 | 0 | 0.01 | 0 | 0 |
| Peptococcaceae | 0.03 | 0.03 | 0.06 | 0.06 | 0.05 | 0.05 | 0 | 0 |
| Thermoanaerobacteraceae | 0.01 | 0.01 | 0.02 | 0.06 | 0.01 | 0.09 | 0 | 0 |
| Victivallaceae | 0.01 | 0 | 0.02 | 0 | 0.01 | 0 | 0 | 0 |
| vadinBE97 | 0.01 | 0 | 0.03 | 0 | 0.01 | 0 | 0 | 0 |
| Acidaminococcaceae | 0 | 0 | 0 | 0 | 0 | 0 | 0.01 | 0.03 |
| Synergistaceae | 0 | 0 | 0.01 | 0 | 0.02 | 0.02 | 0 | 0 |
| Rhodospirillaceae | 0.28 | 0.03 | 0.44 | 0.09 | 0.64 | 0.49 | 0 | 0 |
| Oxalobacteraceae | 0.02 | 0.02 | 0.03 | 0.03 | 0.06 | 0.06 | 0 | 0 |
| Flavobacteriaceae | 0.14 | 0.11 | 0.29 | 0.35 | 0.26 | 0.65 | 0 | 0 |
| Enterococcaceae | 0.02 | 0.12 | 0.05 | 0.96 | 0 | 0.03 | 0 | 0 |
| Bacteroidaceae | 23.67 | 24.69 | 11.81 | 12.21 | 16.37 | 15.22 | 24.67 | 8.77 |
| Rikenellaceae | 3.29 | 4.34 | 6.87 | 12.45 | 5.09 | 14.15 | 3.3 | 1.81 |
| Coriobacteriaceae | 0.98 | 0.59 | 1 | 1.28 | 1.37 | 1.2 | 1.19 | 4.11 |
| Erysipelotrichaceae | 0.05 | 0.08 | 0.04 | 0.47 | 0.03 | 0.23 | 0.03 | 0.02 |
| Porphyromonadaceae | 2.93 | 3.33 | 5.42 | 6.57 | 5.26 | 9.36 | 7.5 | 5.8 |
| Ruminococcaceae | 36.41 | 30.07 | 39.9 | 24.56 | 37.94 | 24.97 | 33.74 | 38.13 |
| Bifidobacteriaceae | 1.23 | 3.36 | 1.65 | 4.57 | 1.46 | 1.91 | 1.68 | 9.16 |
| Prevotellaceae | 0.31 | 0.32 | 0.81 | 0.36 | 0.21 | 0.15 | 0.02 | 0 |
| Veillonellaceae | 1.46 | 1.06 | 2.25 | 3.08 | 2.44 | 1.79 | 2.53 | 3.62 |
| Lachnospiraceae | 16.62 | 17.71 | 13.11 | 16.06 | 10.89 | 15.87 | 22.94 | 26.52 |
| Clostridiaceae 1 | 0.38 | 1.14 | 1.48 | 3.63 | 0.83 | 1.83 | 0.46 | 0.6 |
| Pasteurellaceae | 0.01 | 0.01 | 0 | 0 | 0 | 0 | 0.01 | 0.04 |
| Peptostreptococcaceae | 0.13 | 0.51 | 0.12 | 1.38 | 0.22 | 1.29 | 0.28 | 0.78 |
| Clostridiales vadinBB60 group | 0.99 | 0.13 | 2.61 | 0.51 | 4.06 | 1.16 | 0.1 | 0 |
| Alcaligenaceae | 0.99 | 0.21 | 0.36 | 0.06 | 0.26 | 0.1 | 1.23 | 0.25 |
| Christensenellaceae | 6.52 | 7.87 | 7.38 | 8.81 | 9.01 | 7.52 | 0.07 | 0.07 |
| Family XIII | 0.16 | 0.12 | 0.44 | 0.54 | 0.45 | 0.63 | 0.08 | 0.18 |
| Enterobacteriaceae | 2.94 | 3.61 | 2.75 | 0.98 | 1.86 | 0.16 | 0.06 | 0.05 |
| Verrucomicrobiaceae | 0.05 | 0.13 | 0.07 | 0.14 | 0.11 | 0.17 | 0.03 | 0.01 |
| Streptococcaceae | 0.02 | 0.04 | 0.05 | 0.32 | 0.08 | 0.24 | 0 | 0.02 |
| Desulfovibrionaceae | 0.18 | 0.17 | 0.28 | 0.19 | 0.44 | 0.23 | 0 | 0 |

TABLE 14

Relative abundances (in %) of main genera identified in 4 stools (identified SF) and corresponding inocula (identified IN)

| | S322_IN OC | S322E_ SF | S325_IN OC | S325_ SF | S327_IN OC | S327_ SF | S328_IN OC | S328_ SF |
|---|---|---|---|---|---|---|---|---|
| Tyzzerella 3 | 0 | 0 | 0 | 0 | 0 | 0 | 0 | 0 |
| Lachnospiraceae UCG-003 | 0 | 0 | 0 | 0 | 0 | 0 | 0 | 0 |
| Howardella | 0 | 0 | 0 | 0 | 0 | 0 | 0.01 | 0.02 |
| *Fusobacterium* | 0.01 | 0.01 | 0 | 0 | 0.03 | 0 | 0 | 0 |
| Catenisphaera | 0 | 0.02 | 0 | 0.03 | 0 | 0.01 | 0 | 0 |
| Butyrivibrio | 0 | 0 | 2.31 | 0.77 | 2.05 | 0.43 | 0 | 0 |
| *Ruminococcus* 2 | 0 | 0 | 0 | 0 | 0.07 | 0.14 | 0.5 | 1.07 |
| [*Eubacterium*] *xylanophilum* group | 0.34 | 0.13 | 0.08 | 0.03 | 0.17 | 0.15 | 0 | 0 |
| Lachnospiraceae NK4B4 group | 0.13 | 0.12 | 0.06 | 0.05 | 0.02 | 0.02 | 0 | 0 |
| *Slackia* | 0.02 | 0.12 | 0.03 | 0.34 | 0.02 | 0.13 | 0 | 0 |
| Odoribacter | 0.83 | 0.97 | 2.77 | 3.22 | 2.79 | 5.64 | 0 | 0 |
| Ruminiclostridium | 0.03 | 0.01 | 0.05 | 0.02 | 0.05 | 0.03 | 0 | 0 |
| Senegalimassilia | 0.01 | 0.02 | 0 | 0.04 | 0.01 | 0.04 | 0 | 0 |
| Defluviitaleaceae UCG-011 | 0.02 | 0.02 | 0.02 | 0.02 | 0.03 | 0.02 | 0 | 0 |
| [*Eubacterium*] *oxidoreducens* group | 0.03 | 0.01 | 0.01 | 0.01 | 0.01 | 0.01 | 0 | 0 |
| [*Eubacterium*] *nodatum* group | 0.02 | 0.02 | 0.03 | 0.04 | 0.02 | 0.03 | 0 | 0 |
| *Gelria* | 0.01 | 0.01 | 0.02 | 0.06 | 0.01 | 0.09 | 0 | 0 |
| *Victivallis* | 0.01 | 0 | 0.02 | 0 | 0.01 | 0 | 0 | 0 |
| Ruminococcaceae UCG-007 | 0 | 0 | 0.01 | 0.01 | 0 | 0.01 | 0 | 0 |
| Anaerofilum | 0.01 | 0.01 | 0.01 | 0 | 0.01 | 0.01 | 0 | 0 |
| uncultured rumen bacterium | 0.01 | 0 | 0.03 | 0 | 0.01 | 0 | 0 | 0 |
| Eisenbergiella | 0 | 0 | 0.03 | 0 | 0.02 | 0 | 0 | 0 |
| *Acidaminococcus* | 0 | 0 | 0 | 0 | 0 | 0 | 0.01 | 0.03 |
| *Shuttleworthia* | 0.01 | 0.01 | 0.01 | 0.04 | 0.0 | 0.1 | 0 | 0 |
| *Synergistes* | 0 | 0 | 0.01 | 0 | 0.02 | 0.02 | 0 | 0 |
| Oscillibacter | 0.02 | 0.01 | 0.03 | 0.01 | 0.03 | 0.02 | 0 | 0 |
| Ruminococcaceae UCG-011 | 0.02 | 0.03 | 0.02 | 0.03 | 0.02 | 0.06 | 0 | 0 |
| Hydrogenoanaerobacterium | 0.03 | 0.02 | 0.13 | 0.06 | 0.12 | 0.06 | 0 | 0 |
| Oxalobacter | 0.02 | 0.02 | 0.03 | 0.03 | 0.06 | 0.06 | 0 | 0 |
| [*Ruminococcus*] *gnavus* group | 0 | 0 | 0 | 0 | 0 | 0 | 0.08 | 0.07 |
| *Desulfovibrio* | 0.11 | 0.13 | 0.17 | 0.18 | 0.24 | 0.17 | 0 | 0 |
| Parasutterella | 0.2 | 0.11 | 0.1 | 0.05 | 0.15 | 0.06 | 0 | 0 |
| Enterococcus | 0.02 | 0.12 | 0.05 | 0.96 | 0 | 0.03 | 0 | 0 |
| [*Eubacterium*] *fissicatena* group | 0 | 0 | 0 | 0 | 0.22 | 0.94 | 0.03 | 0 |
| Ruminococcaceae UCG-003 | 0.22 | 0.13 | 0.03 | 0.05 | 0.06 | 0.06 | 0 | 0 |
| *Butyricimonas* | 0.25 | 0.2 | 0.44 | 0.57 | 0.32 | 0.53 | 0 | 0 |
| *Streptococcus* | 0 | 0.02 | 0.01 | 0.05 | 0.02 | 0.03 | 0 | 0.01 |
| Ruminococcaceae UCG-010 | 0.63 | 0.47 | 1.21 | 0.71 | 1.33 | 1.07 | 0 | 0 |
| Bacteroides | 23.66 | 24.68 | 11.8 | 12.2 | 16.35 | 15.2 | 24.67 | 8.77 |
| Alistipes | 3.29 | 4.34 | 6.87 | 12.45 | 5.09 | 14.15 | 3.3 | 1.81 |
| Ruminiclostridium 5 | 0.11 | 0.13 | 0.22 | 0.47 | 0.17 | 0.35 | 0.11 | 0.22 |
| Hafnia-Obesumbacterium | 0.32 | 0.29 | 1.04 | 0.75 | 0 | 0 | 0.01 | 0 |
| [*Eubacterium*] *eligens* group | 1.01 | 0.36 | 1.08 | 0.18 | 0.52 | 0.13 | 1.2 | 0.13 |
| Terrisporobacter | 0.0 | 0.06 | 0 | 0.02 | 0 | 0.02 | 0.05 | 0.24 |
| *Roseburia* | 0.36 | 0.39 | 0.17 | 0.18 | 0.34 | 0.45 | 4.79 | 2.82 |
| Coprobacter | 0.19 | 0.22 | 0.1 | 0.06 | 0.23 | 0.23 | 0.07 | 0.02 |
| Lachnospiraceae FCS020 group | 0.13 | 0.17 | 0.04 | 0.03 | 0.04 | 0.01 | 0.05 | 0.08 |
| Bilophila | 0.06 | 0.04 | 0.08 | 0.01 | 0.18 | 0.06 | 0 | 0 |
| Lachnoclostridium | 0.16 | 0.11 | 0.17 | 0.01 | 0.22 | 0.04 | 0.28 | 0.09 |
| *Collinsella* | 0.91 | 0.24 | 0.91 | 0.57 | 1.28 | 0.57 | 1.14 | 3.97 |
| Erysipelotrichaceae UCG-003 | 0.03 | 0.05 | 0.01 | 0.25 | 0.01 | 0.16 | 0.03 | 0.02 |
| [*Eubacterium*] *coprostanoligenes* group | 2.23 | 0.94 | 2.43 | 2.25 | 2.02 | 1.75 | 3.64 | 4.06 |
| Lachnospiraceae UCG-004 | 0.58 | 0.07 | 0.15 | 0.03 | 0.09 | 0.03 | 0.46 | 0.01 |
| Ruminiclostridium 9 | 0.18 | 0.07 | 0.16 | 0.07 | 0.17 | 0.15 | 0.43 | 0.03 |
| Ruminococcaceae UCG-004 | 0 | 0 | 0.01 | 0.01 | 0.01 | 0.01 | 0.1 | 0.07 |
| *Coprococcus* 2 | 1.71 | 1.14 | 0.44 | 1.26 | 2.41 | 2.58 | 1.04 | 0.21 |
| Turicibacter | 0 | 0 | 0.02 | 0.18 | 0.02 | 0.07 | 0 | 0 |
| Family XIII UCG-001 | 0.05 | 0.01 | 0.01 | 0.01 | 0.01 | 0.04 | 0.07 | 0.16 |
| Parabacteroides | 0.86 | 0.96 | 0.65 | 0.95 | 0.77 | 1.16 | 5.3 | 4.39 |
| [*Ruminococcus*] *gauvreauii* group | 0.01 | 0.04 | 0.04 | 0.07 | 0.02 | 0.05 | 0.01 | 0.07 |
| Lachnospiraceae UCG-008 | 0.07 | 0.06 | 0.04 | 0.06 | 0.05 | 0.06 | 0.03 | 0.06 |
| Oscillospira | 0.1 | 0.03 | 0.07 | 0.03 | 0.12 | 0.07 | 0.08 | 0 |
| Faecalibacterium | 14.35 | 11.08 | 14.11 | 3.53 | 11.21 | 4.61 | 15.46 | 20.56 |
| Blautia | 2.94 | 2.83 | 1.44 | 2.5 | 0.8 | 2.25 | 0.51 | 1.5 |

TABLE 14-continued

Relative abundances (in %) of main genera identified in 4 stools
(identified SF) and corresponding inocula (identified IN)

| | S322_IN_OC | S322E_SF | S325_IN_OC | S325_SF | S327_IN_OC | S327_SF | S328_IN_OC | S328_SF |
|---|---|---|---|---|---|---|---|---|
| Bifidobacterium | 1.23 | 3.36 | 1.65 | 4.55 | 1.46 | 1.91 | 1.67 | 9.11 |
| Paraprevotella | 0.31 | 0.32 | 0.81 | 0.36 | 0.21 | 0.15 | 0.02 | 0 |
| Ruminococcaceae UCG-005 | 2.24 | 1.42 | 2.52 | 1.73 | 2.84 | 1.8 | 0.34 | 0.1 |
| Lachnospiraceae UCG-010 | 0.03 | 0.01 | 0.01 | 0.01 | 0.01 | 0.01 | 0.03 | 0 |
| Adlercreutzia | 0 | 0.01 | 0.01 | 0.01 | 0 | 0.02 | 0.01 | 0.04 |
| Dialister | 1.4 | 0.97 | 2.14 | 2.77 | 2.35 | 1.64 | 2.53 | 3.62 |
| Fusicatenibacter | 0.55 | 0.67 | 1.28 | 0.7 | 0.35 | 0.24 | 0.41 | 0.64 |
| *Dorea* | 0.52 | 1 | 0.22 | 0.44 | 0.17 | 0.37 | 1.45 | 3.48 |
| [*Eubacterium*] *rectale* group | 2.13 | 4.81 | 3.61 | 2.61 | 1.68 | 1.23 | 5.25 | 11.71 |
| Intestinimonas | 0.01 | 0 | 0.01 | 0 | 0.01 | 0 | 0.07 | 0 |
| *Sarcina* | 0.35 | 1.02 | 1.47 | 3.45 | 0.8 | 1.66 | 0.01 | 0.01 |
| Haemophilus | 0.01 | 0.01 | 0 | 0 | 0 | 0 | 0.01 | 0.04 |
| *Anaerostipes* | 0.44 | 0.66 | 0.13 | 2.97 | 0.13 | 3.78 | 0.42 | 0.34 |
| Lachnospiraceae NC2004 group | 0.01 | 0.01 | 0.01 | 0.01 | 0.01 | 0 | 0.03 | 0.07 |
| Intestinibacter | 0.12 | 0.44 | 0.12 | 1.35 | 0.21 | 1.25 | 0.23 | 0.51 |
| Ruminococcaceae UCG-002 | 1.66 | 1.35 | 2.64 | 2.41 | 3.29 | 3.96 | 1.2 | 0.33 |
| Ruminococcaceae UCG-014 | 6.25 | 6.85 | 7.67 | 7.89 | 7.26 | 4.69 | 5.34 | 7.29 |
| *Ruminococcus* 1 | 1.96 | 0.92 | 1.06 | 0.49 | 1.1 | 0.55 | 3.7 | 1.64 |
| *Clostridium* sensu stricto 1 | 0.03 | 0.12 | 0.01 | 0.18 | 0.04 | 0.17 | 0.45 | 0.59 |
| Marvinbryantia | 0.02 | 0.04 | 0.08 | 0.04 | 0.08 | 0.06 | 0 | 0.02 |
| [*Eubacterium*] *hallii* group | 0.08 | 0.9 | 0.12 | 1.66 | 0.11 | 1.31 | 0.08 | 0.98 |
| *Lachnospira* | 1.7 | 0.07 | 0.07 | 0.04 | 0.12 | 0.02 | 2.91 | 0.57 |
| Ruminococcaceae UCG-009 | 0.04 | 0.01 | 0.02 | 0 | 0.01 | 0.01 | 0.05 | 0.0 |
| [*Ruminococcus*] *torques* group | 0.47 | 0.7 | 0.36 | 0.47 | 0.17 | 0.45 | 0.92 | 1.72 |
| Ruminiclostridium 6 | 1.4 | 1.31 | 0.13 | 0.08 | 0.25 | 0.17 | 0.01 | 0 |
| *Sutterella* | 0.79 | 0.1 | 0.26 | 0.01 | 0.11 | 0.03 | 1.23 | 0.25 |
| Christensenellaceae R-7 group | 6.47 | 7.82 | 7.33 | 8.79 | 8.98 | 7.5 | 0.07 | 0.07 |
| Barnesiella | 0.46 | 0.71 | 0.57 | 1.42 | 0.61 | 1.48 | 0.86 | 0.47 |
| Ruminococcaceae NK4A214 group | 0.71 | 0.5 | 0.71 | 0.77 | 0.99 | 1.53 | 0.01 | 0 |
| *Coprococcus* 3 | 0.56 | 1.39 | 0.19 | 0.56 | 0.17 | 0.21 | 0.27 | 0.35 |
| Ruminococcaceae UCG-013 | 0.31 | 0.42 | 0.21 | 0.6 | 0.25 | 0.39 | 0.49 | 0.8 |
| Lachnospiraceae UCG-001 | 1.61 | 0.85 | 0.05 | 0.05 | 0.04 | 0.02 | 0.52 | 0.02 |
| Family XIII AD3011 group | 0.09 | 0.09 | 0.41 | 0.48 | 0.42 | 0.57 | 0 | 0.02 |
| [*Eubacterium*] *ventriosum* group | 0.26 | 0.43 | 0.3 | 0.45 | 0.26 | 0.2 | 0.45 | 0.3 |
| *Subdoligranulum* | 1.93 | 2.72 | 3.27 | 1.96 | 3.51 | 1.9 | 0.91 | 1.2 |
| Lachnospiraceae NK4A136 group | 0.26 | 0.15 | 0.03 | 0.01 | 0.11 | 0.07 | 1.29 | 0.85 |
| *Coprococcus* 1 | 0.14 | 0.09 | 0.11 | 0.19 | 0.09 | 0.2 | 0.1 | 0.05 |
| Peptoclostridium | 0 | 0.01 | 0 | 0.01 | 0 | 0.01 | 0.01 | 0.03 |
| Escherichia-Shigella | 2.62 | 3.31 | 1.71 | 0.23 | 1.86 | 0.16 | 0.06 | 0.04 |
| Butyricicoccus | 0.26 | 0.31 | 0.12 | 0.17 | 0.02 | 0.02 | 0.21 | 0.4 |
| Anaerotruncus | 0.34 | 0.3 | 0.19 | 0.12 | 0.31 | 0.3 | 0.11 | 0.04 |
| Akkermansia | 0.05 | 0.13 | 0.07 | 0.14 | 0.11 | 0.17 | 0.03 | 0.01 |
| *Lactococcus* | 0.01 | 0.03 | 0.04 | 0.27 | 0.06 | 0.21 | 0 | 0.01 |

Furthermore, inocula produced with the process described were used to inoculate axenic mice. The fresh microbiota used to prepare the frozen samples was also inoculated to axenic mice. Data presented in WO 2016/170285 (A1) show that excellent consistency was found between the genera observed in fresh stool inoculated mice and processed stools inoculated mice. More particularly, *Facelibacterium* genus, known to be very sensitive to aerobic conditions, did colonize the mice gut at the same level for both groups, whereas in a control group inoculated with NaCl-processed microbiota, *Faecalibacterium* did not succeed to colonize. On the contrary, *Bacteroides* genus overgrew in NaCl group where it was found at a similar level in both fresh and processed stools inoculated mice. The conclusion was that the process described in WO 2016/170285 (A1) allowed an excellent recovery of the main genera present in the collected stool.

REFERENCES

Alexander, J. L. et al. (2017) 'Gut microbiota modulation of chemotherapy efficacy and toxicity', Nature Reviews Gastroenterology and Hepatology. Nature Publishing Group, 14(6), pp. 356-365. doi: 10.1038/nrgastro.2017.20.

Artz, A. S. et al. (2008) 'Pre-treatment C-reactive Protein (CRP) is a Predictor for Allogeneic Hematopoietic Cell Transplantation Outcomes', Biology of blood and marrow transplantation: journal of the American Society for Blood and Marrow Transplantation, 14(11), p. 1209. doi: 10.1016/j.bbmt.2008.08.004.Pre-treatment.

Bolger, A. M., Lohse, M. and Usadel, B. (2014) 'Trimmomatic: A flexible trimmer for Illumina sequence data', Bioinformatics, 30(15), pp. 2114-2120. doi: 10.1093/bioinformatics/btu170.

Camera, A. et al. (2003) 'Intestinal toxicity during induction chemotherapy with cytarabine-based regimens in adult acute myeloid leukemia', Hematology Journal, 4(5), pp. 346-350. doi: 10.1038/sj.thj.6200304.

Derrien, M., Belzer, C. and de Vos, W. M. (2017) 'Akkermansia muciniphila and its role in regulating host functions', Microbial Pathogenesis. Elsevier Ltd, 106, pp. 171-181. doi: 10.1016/j.micpath.2016.02.005.

Döhner, H., Weisdorf, D. J. and D, B. C. (2015) 'Acute Myeloid Leukemia', The New England Journal of Medicine, 373(12), pp. 1136-52. doi: 10.1056/NEJMra1406184.

Elting, L. S. et al. (2003) 'The burdens of cancer therapy: Clinical and economic outcomes of chemotherapy-induced mucositis', Cancer, 98(7), pp. 1531-1539. doi: 10.1002/cncr.11671.

Galloway-Pena, J. R. et al. (2016) 'The role of the gastrointestinal microbiome in infectious complications during induction chemotherapy for acute myeloid leukemia', Cancer, 122(14), pp. 2186-2196. doi: 10.1002/cncr.30039.

Galloway-Peña, J. R. et al. (2017) 'Characterization of oral and gut microbiome temporal variability in hospitalized cancer patients', Genome Medicine. Genome Medicine, 9(1), pp. 1-14. doi: 10.1186/s13073-017-0409-1.

Hogan, W. J. et al. (2002) 'Neutropenic colitis after treatment of acute myelogenous leukemia with idarubicin and cytosine arabinoside', Mayo Clinic Proceedings, 77(8), pp. 760-762. doi: 10.4065/77.8.760.

Hong, J. et al. (2015) 'Pre-treatment blood inflammatory markers as predictors of systemic infection during induction chemotherapy: results of an exploratory study in patients with acute myeloid leukemia', Supportive Care in Cancer, 24(1), pp. 187-194. doi: 10.1007/s00520-015-2762-1.

Iida, N. et al. (2013) 'Commensal bacteria control cancer response to therapy by modulating the tumor microenvironment', Science, 342(6161), pp. 967-970. doi: 10.1126/science.1240527.

Jandhyala, S. M. et al. (2015) 'Role of the normal gut microbiota', World Journal of Gastroenterology, 21(29), pp. 8836-8847. doi: 10.3748/wjg.v21.i29.8787.

Jenq, R. R. et al. (2015) 'Intestinal *Blautia* is associated with reduced death from graft-versus-host disease', Biol Blood Marrow Transplant., 21(8), pp. 1373-1383. doi: 10.1016/j.cogdev.2010.08.003.Personal.

Khanna, S. (2018) 'Microbiota Replacement Therapies: Innovation in Gastrointestinal Care', Clinical Pharmacology and Therapeutics, 103(1), pp. 102-111. doi: 10.1002/cpt.923.

Khitam A W Ali, Alaa F Alwan, H. A. M. (2015) 'C-Reactive protein and iron status in Iraqi patients with acute myeloid leukemia before and after treatment', Iraqi J. Hematology.

Langmead, Ben and Salzberg, S. (2013) 'Fast gapped-read alignment with Bowtie2', Nature methods, 9(4), pp. 357-359. doi: 10.1038/nmeth.1923.Fast.

Lehouritis, P. et al. (2015) 'Local bacteria affect the efficacy of chemotherapeutic drugs', Scientific Reports. Nature Publishing Group, 5, pp. 1-12. doi: 10.1038/srep14554.

Li, J. et al. (2014) 'An integrated catalog of reference genes in the human gut microbiome', Nature Biotechnology, 32(8), pp. 834-841. doi: 10.1038/nbt.2942.

Malard, F. et al. (2018) 'High gastrointestinal microbial diversity and clinical outcome in graft-versus-host disease patients', Bone Marrow Transplantation. Springer US. doi: 10.1038/s41409-018-0254-x.

Mayer, K. et al. (2015) 'Comparison of antibiotic prophylaxis with cotrimoxazole/colistin (COT/COL) versus ciprofloxacin (CIP) in patients with acute myeloid leukemia', Supportive Care in Cancer, 23(5), pp. 1321-1329. doi: 10.1007/s00520-015-2621-0.

Montassier, E. et al. (2015) 'Alimentary Pharmacology and Therapeutics Chemotherapy-driven dysbiosis in the intestinal microbiome', (July). doi: 10.1111/apt.13302.

Nancey, S. et al. (2013) 'Neopterin is a novel reliable fecal marker as accurate as calprotectin for predicting endoscopic disease activity in patients with inflammatory bowel diseases', Inflammatory Bowel Diseases, 19(4), pp. 1043-1052. doi: 10.1097/MIB.0b013e3182807577.

Palm, N. W., Zoete, M. R. De and Flavell, R. A. (2015) 'Immune-microbiota interactions in health and disease', Clinical Immunology, 159, pp. 122-127. doi: 10.1016/j.clim.2015.05.014.

Routy, B. et al. (2018) 'Gut microbiome influences efficacy of PD-1{\textendash}based immunotherapy against epithelial tumors', Science, 359(6371), pp. 91-97. doi: 10.1126/science.aan3706.

Roy, S. and Trinchieri, G. (2017) 'Microbiota: A key orchestrator of cancer therapy', Nature Reviews Cancer. Nature Publishing Group, 17(5), pp. 271-285. doi: 10.1038/nrc.2017.13.

Saultz, J. and Garzon, R. (2016) 'Acute Myeloid Leukemia: A Concise Review', Journal of Clinical Medicine, 5(3), p. 33. doi: 10.3390/jcm5030033.

Sokol, H. et al. (2008) '*Faecalibacterium prausnitzii* is an anti-inflammatory commensal bacterium identified by gut microbiota analysis of Crohn disease patients', Proceedings of the National Academy of Sciences, 105(43), pp. 16731-16736. doi: 10.1073/pnas.0804812105.

Steck, N. et al. (2011) '*Enterococcus faecalis* metalloprotease compromises epithelial barrier and contributes to intestinal inflammation', Gastroenterology. Elsevier Inc., 141(3), pp. 959-971. doi: 10.1053/j.gastro.2011.05.035.

Strickertsson, J. A. B. et al. (2013) '*Enterococcus faecalis* Infection Causes Inflammation, Intracellular Oxphos-Independent ROS Production, and DNA Damage in Human Gastric Cancer Cells', PLoS ONE, 8(4). doi: 10.1371/journal.pone.0063147.

Taur, Y. et al. (2014) 'The effects of intestinal tract bacterial diversity on mortality following allogeneic hematopoietic stem cell transplantation', Transplantation, 124(7), pp. 1174-1182. doi: 10.1182/blood-2014-02-554725.The.

Weiss, G. A. and Hennet, T. (2017) 'Mechanisms and consequences of intestinal dysbiosis', Cellular and Molecular Life Sciences. Springer International Publishing, 74(16), pp. 2959-2977. doi: 10.1007/s00018-017-2509-x.

Wu, R. et al. (2017) 'Significance of serum total oxidant/antioxidant status in patients with colorectal cancer', PLoS ONE, 12(1), pp. 1-13. doi: 10.1371/journal.pone.0170003.

The invention claimed is:

1. A method for reducing an inflammation induced by anti-cancer therapy combined with antibiotherapy and/or hematopoietic stem cell transplantation (HSCT) in acute leukemia patients, comprising administering a human fecal microbiota composition to the individual,
  wherein the proportion of some or all the following 15 genera is increased relative to the level before a fecal microbiota transfer (FMT): *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio*; and
  wherein neopterin in a gut, C-Reactive Protein (CRP) in serum and/or ferritin in serum is decreased, wherein the human fecal microbiota composition administered comprises some or all the following 15 genera: *Blautia, Faecalibacterium, Alistipes, Eubacterium, Bifidobacterium, Ruminococcus, Clostridium, Coprococcus, Odoribacter, Roseburia, Holdemanella, Anaerostipes, Oscillibacter, Subdoligranulum* and *Butyrivibrio;* and wherein neopterin in a gut, C-Reactive Protein (CRP) in serum and/or ferritin in serum is decreased.

2. The method of claim 1, wherein, in step (ii) the aqueous saline solution comprises at least a cryoprotectant and a bulking agent.

3. The method of claim 1, wherein the human fecal microbiota composition comprises microbiota from one or several stool samples from the individual.

4. The method of claim 3, wherein the human fecal microbiota composition comprises at least 90% of the species present in the at least one sample from the individual.

5. The method of claim 1, wherein the inflammation induced by anti-cancer therapy combined with antibiotherapy and/or hematopoietic stem cell transplantation (HSCT) is a gut inflammation.

6. The method of claim 1, wherein at least one fecal microbiota transfer (FMT) is performed 1 to 30 days after the end of the anti-cancer therapy.

7. The method of claim 6, wherein two FMT are performed in a 1-7-days interval.

8. The method of claim 6, wherein FMT with said human fecal microbiota composition leads to an increase of the proportion of beneficial bacteria and a decrease of the proportion of deleterious bacteria in the gastrointestinal tract.

9. The method of claim 1, wherein said individual has acute myeloid leukemia.

10. The method of claim 1, wherein the human fecal microbiota composition is administered before, during and/or after anti-cancer therapy.

11. The method of claim 1, wherein the fecal microbiota composition has been obtained by a process comprising the steps of:

(i) collecting a stool sample and putting it in anaerobic conditions at most 5 minutes after collection;

(ii) still in anaerobic conditions, mixing the sample with an aqueous saline solution comprising at least a cryoprotectant and/or a bulking agent; and (iii) filtering the diluted sample.

12. The method of claim 11, wherein, in step (ii) the aqueous saline solution comprises at least a cryoprotectant and a bulking agent.

13. The method of claim 8, wherein the beneficial bacteria comprise bacteria belonging to the Lachnospiraceae, Ruminococcaceae, Bifidobacteriaceae, Streptococcaceae, Akkermansiaceae, Lactobacilliae, Eubacteriaceae, Erysipelotrichaceae, Eggerthellaceae, Clostridiaceae, Prevotellaceae, Oscillospiraceae, Rikenellaceae and/or Odoribacteraceae families.

14. The method of claim 8, wherein the deleterious bacteria comprise bacteria belonging to the *Bacteroidaceae* and/or *Enterococcaceae* families.

15. The method of claim 1, wherein the proportion of *Faecalibacterium* increases and the proportion of *Bacteroides* decreases relative to the level before a fecal microbiota transfer (FMT).

16. The method of claim 1, wherein a fecal microbiota transfer (FMT) leads to a decrease of neopterin in a gut by at least 10%, at least 20%, at least 30% or at least 40%.

17. The method of claim 1, wherein a fecal microbiota transfer (FMT) leads to a decrease of seric level of CRP by at least 10%, at least 20%, at least 30% or at least 40%.

18. The method of claim 1, wherein a fecal microbiota transfer (FMT) leads to a decrease of seric level of ferritin by at least 10%, at least 20%, at least 30% or at least 40%.

19. The method of claim 1, wherein the fecal microbiota composition administered comprises some or all the following genera: *Blautia, Faecalibacterium, Alistipes, Eubacterium, Bifidobacterium, Clostridium, Coprococcus, Odoribacter, Roseburia, Anaerostipes, Oscillibacter,* and *Subdoligranulum.*

* * * * *